United States Patent
Tanner et al.

(10) Patent No.: US 10,459,212 B2
(45) Date of Patent: Oct. 29, 2019

(54) OPTICAL TRAP FOR RHEOLOGICAL CHARACTERIZATION OF BIOLOGICAL MATERIALS

(71) Applicant: The United States of America, as represented by the Secretary, Department of Health and Human Services, Bethesda, MD (US)

(72) Inventors: Kandice Tanner, Rockville, MD (US); Benjamin Blehm, Oro Valley, AZ (US); Alexus Devine, Bethesda, MD (US)

(73) Assignee: The United States of America, as represented by the Secretary, Dept. of Health and Human Service, Bethesda, MD (US)

( * ) Notice: Subject to any disclaimer, the term of this patent is extended or adjusted under 35 U.S.C. 154(b) by 99 days.

(21) Appl. No.: 15/744,672

(22) PCT Filed: Jul. 29, 2016

(86) PCT No.: PCT/US2016/044850
§ 371 (c)(1),
(2) Date: Jan. 12, 2018

(87) PCT Pub. No.: WO2017/020006
PCT Pub. Date: Feb. 2, 2017

(65) Prior Publication Data
US 2018/0202913 A1    Jul. 19, 2018

Related U.S. Application Data

(60) Provisional application No. 62/198,554, filed on Jul. 29, 2015.

(51) Int. Cl.
*G02B 21/32* (2006.01)
*G01N 11/16* (2006.01)
(Continued)

(52) U.S. Cl.
CPC ............ *G02B 21/32* (2013.01); *A61B 5/0091* (2013.01); *A61B 5/445* (2013.01); *G01N 11/00* (2013.01);
(Continued)

(58) Field of Classification Search
CPC ................. G01N 11/00; G01N 11/16; G01N 2203/0089; G01N 2203/0094; G02B 21/32
See application file for complete search history.

(56) References Cited

U.S. PATENT DOCUMENTS

| 5,486,457 A | 1/1996 | Butler et al. |
|---|---|---|
| 7,800,750 B2 | 9/2010 | Bustamante et al. |

(Continued)

OTHER PUBLICATIONS

Blehm, et al. "In vivo tissue has non-linear rheological behavior distinct from 3D biomimetic hydrogels, as determined by AMOTIV microscopy," *Biomaterials*, 83:66-78, 2016.
(Continued)

*Primary Examiner* — Maurice C Smith
(74) *Attorney, Agent, or Firm* — Klarquist Sparkman, LLP

(57) ABSTRACT

Systems and methods for assaying the viscoelastic properties of a heterogeneous material are provided. The systems and methods allow for application of an in situ calibrated optical trap to optical trap beads within the material to assay the viscoelastic properties. In several embodiments, the material can be a biological material, such as tumor tissue or skin tissue.

26 Claims, 20 Drawing Sheets

(51) Int. Cl.
*G01N 11/00* (2006.01)
*A61B 5/00* (2006.01)

(52) U.S. Cl.
CPC ........ *G01N 11/16* (2013.01); *G01N 2011/008* (2013.01); *G01N 2203/0089* (2013.01); *G01N 2203/0094* (2013.01)

(56) References Cited

U.S. PATENT DOCUMENTS

| | | | |
|---|---|---|---|
| 7,968,839 | B2 | 6/2011 | Merenda et al. |
| 8,773,538 | B2 | 7/2014 | Lin et al. |
| 8,844,369 | B2 | 9/2014 | Botvinick et al. |
| 2007/0160175 | A1* | 7/2007 | Lang .................. G01N 21/6458 376/103 |
| 2012/0288925 | A1 | 11/2012 | Wang et al. |
| 2014/0150534 | A1 | 6/2014 | Dennin et al. |

OTHER PUBLICATIONS

Brau, et al. "Passive and active microrheology with optical tweezers." *Journal of Optics A: Pure and Applied Optics* 9, No. 8 (2007): S103.

Capitanio, et al. "Interrogating biology with force: single molecule high-resolution measurements with optical tweezers." *Biophysical Journal* 105, No. 6 (2013): 1293-1303.

Elkin, et al. "Mechanical heterogeneity of the rat hippocampus measured by atomic force microscope indentation." *Journal of Neurotrauma* 24, No. 5 (2007): 812-822.

Fabry, et al. "Time scale and other invariants of integrative mechanical behavior in living cells," *Physical Review E*, 68:041914, 2003.

Fabry, et al. "Scaling the microrheology of living cells," *Physical Review Letters*, 87: 148102, 2001.

Fischer, et al. "Calibration of trapping force and response function of optical tweezers in viscoelastic media," *Journal of Optics A: Pure and Applied Optics*, 9:S239-S250, 2007.

Fischer, et al. "Active-passive calibration of optical tweezers in viscoelastic media," *Review of Scientific Instruments*, 81:015103, 2010.

Jun, et al. "Calibration of optical tweezers for in vivo force measurements: How do different approaches compare?" *Biophysical Journal*, 107:1474-1484, 2014.

Keikha, et al. "Multi-frequency technique for frequency response measurement and its application to servo system with friction." *IFAC Proceedings vols.* 44, No. 1 (2011): 5273-5278.

Kim, et al. "Recapitulating the tumor ecosystem along the metastatic cascade using 3D culture models." *Frontiers in Oncology* 5 (2015).

Mas, et al. "Quantitative determination of optical trapping strength and viscoelastic moduli inside living cells," *Physical Biology*, 10:046006, 2013.

Mizuno, et al. "Active and passive microrheology in equilibrium and nonequilibrium systems." *Macromolecules* 41, No. 19 (2008): 7194-7202.

Norregaard, et al. "Optical manipulation of single molecules in the living cell," *Physical Chemistry Chemical Physics*, 16:12614-12624, 2014.

Sarshar, et al. "Comparative study of methods to calibrate the stiffness of a single-beam gradient-force optical tweezers over various laser trapping powers," *Journal of Biomedical Optics*, 19.115001-115001, 2014.

Shindel, et al. "Frequency modulated microrheology," *Lab on a Chip* 15, No. 11 (2015): 2460-2466.

Tassieri. "Linear microrheology with optical tweezers of living cells 'is not an option'!" *Soft Matter*, 11:5792-5798, 2015.

* cited by examiner

Matrigel

HA

Zebrafish Tail

Zebrafish Brain

Microrheology HA

Microrheology HA

Bulk HA

Bulk Matrigel

Zebrafish Beta Cal
Outside Linear Range Scan

Center of Zebrafish Beta Cal
Area of Fitting for Calibration

Single Frequency Oscillation: Slow, comparable to bulk rheology

Multiplexed Oscillation: Fast data acquisition

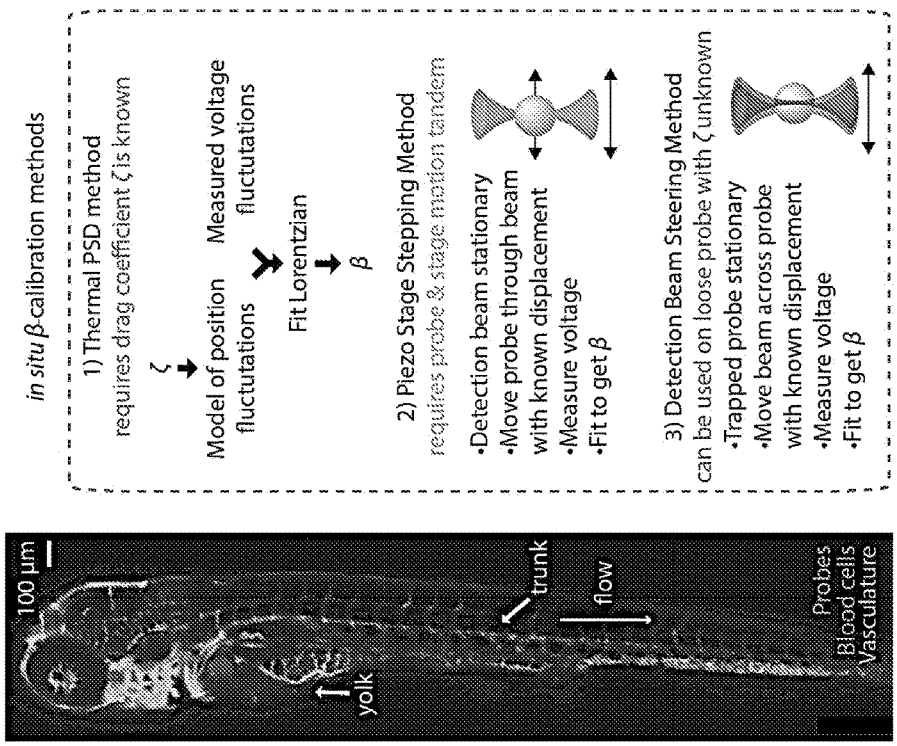
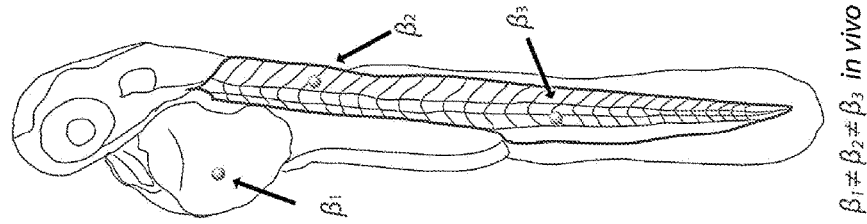
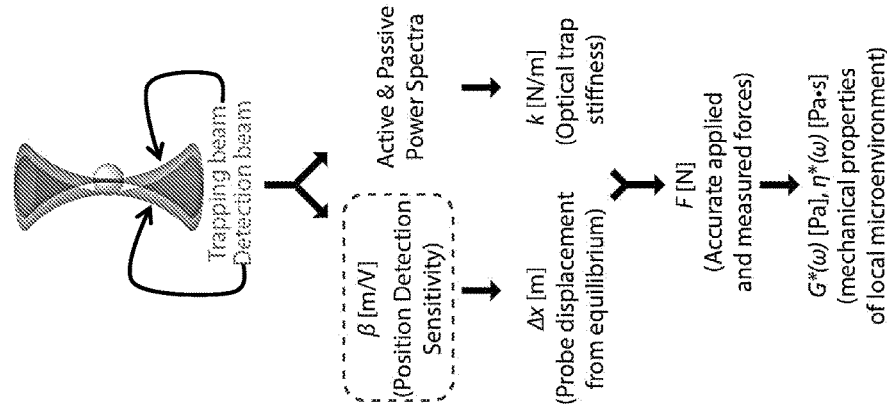
FIG. 13A
FIG. 13B
FIG. 13C

Piezo Stage Stepping Method
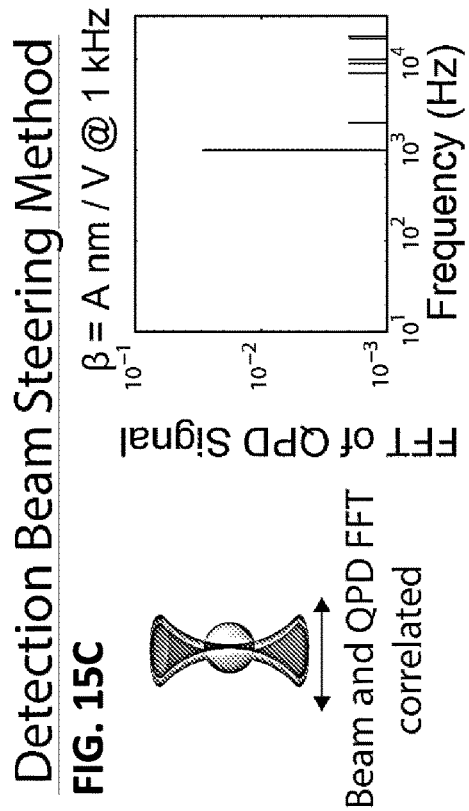
FIG. 15A Probe & stage motion correlated (No flow)
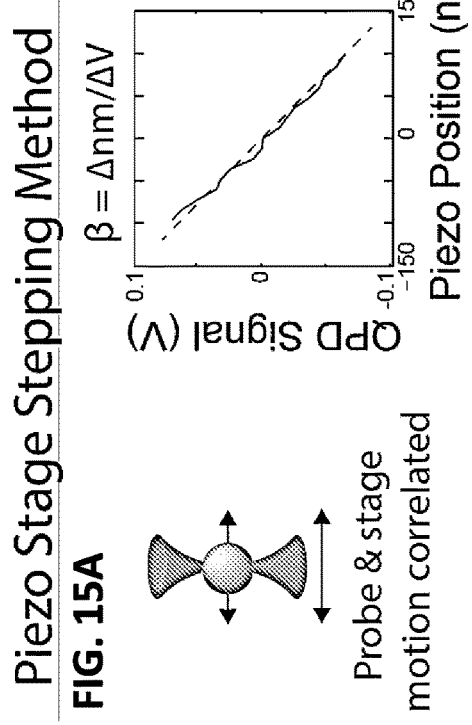
FIG. 15B Probe & stage motion uncorrelated (Flow)
Detection Beam Steering Method
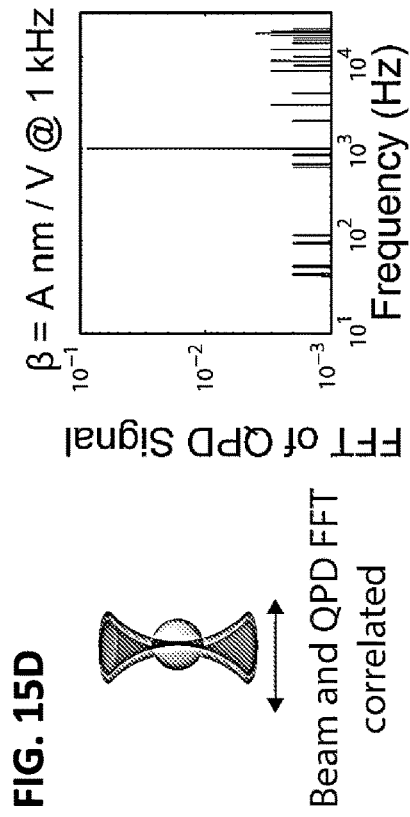
FIG. 15C Beam and QPD FFT correlated (No flow)
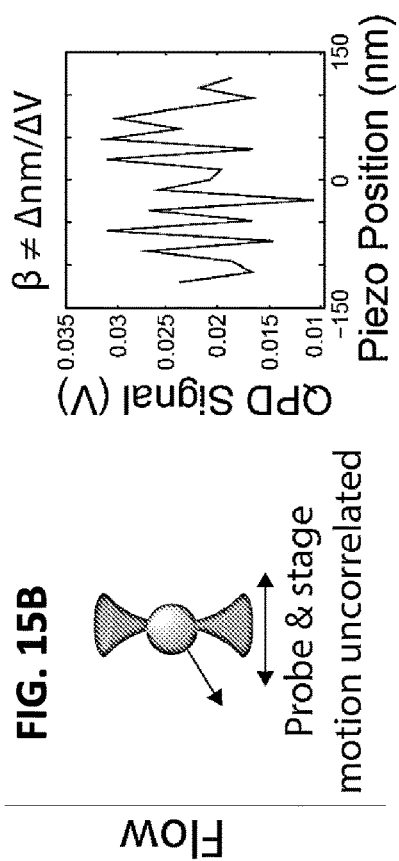
FIG. 15D Beam and QPD FFT correlated (Flow)

OPTICAL TRAP FOR RHEOLOGICAL CHARACTERIZATION OF BIOLOGICAL MATERIALS

CROSS REFERENCE TO RELATED APPLICATIONS

This is the U.S. National Stage of International Application No. PCT/US2016/044850, filed Jul. 29, 2016, which was published in English under PCT Article 21(2), which in turn claims the benefit of U.S. Provisional Application No. 62/198,554, filed Jul. 29, 2015. The provisional application is incorporated by reference herein in its entirety.

FIELD OF THE DISCLOSURE

This relates to embodiments of systems and methods for applying an optical trap to a bead embedded in a sample to assay the viscoelastic properties of the sample.

BACKGROUND

The viscoelastic properties of a material (such as a biological material), are the resistance to flow (viscosity) and the resistance to deformation (elasticity) of the material. Viscous materials resist shear and strain linearly with time upon application of stress. Elastic materials strain when stretched and return to their original state when the stress is removed. Viscoelastic materials have elements of both of these properties and, as such, exhibit time-dependent strain. The storage and loss modulus (the "complex modulus") in viscoelastic materials measure the stored energy, representing the elastic portion, and the energy dissipated as heat, representing the viscous portion. Biological materials are rarely just viscous or just elastic, and typically display a combination of viscoelastic properties.

An optical trap includes a focused laser beam able to trap small particles at its focus, and can be used to interrogate the viscoelastic properties of certain materials. However, issues of image resolution and limited depth of interrogation have prevented use of optical trap techniques to measure viscoelastic properties in certain materials, such as biological materials including multi-cellular systems and tissue in living organisms.

SUMMARY

The methods and systems disclosed herein involve the use of an optical trap to evaluate the viscoelastic properties of a sample, such as a biological material. Using the disclosed systems and methods, it is possible, for the first time, to interrogate the viscoelastic properties of in vivo and ex vivo tissue using optical trap-based microrheology.

In some embodiments, a method of assaying viscoelastic properties of a sample is provided. The sample can be, for example, a biological material, such as a 3D tissue culture sample, an in vivo or ex vivo tissue sample, and/or a tumor sample. The method comprises directing a detection beam to an optical trap bead embedded in the sample, and detecting movement of the bead by sensing a position of the detection beam downstream of the bead. A trap beam is directed on the bead to apply an optical trap to the bead. Passive movement of the trapped bead due to thermal motion is detected. The trapped bead is oscillated relative to the sample with a complex waveform comprising a predetermined combination of frequencies, wherein the bead is oscillated along a plane transverse to a path of the detection beam. The active movement of the trapped bead due to the oscillation is detected. Based on the detected passive movement and the detected active movement, a trap stiffness and a complex modulus for the bead are calculated.

In some embodiments, the complex waveform used to oscillate the bead comprises a combination of frequencies that provide distinct harmonics, such as a set of prime frequencies of from 3 to 101 Hz, for example a set of 20 frequencies of from 3 to 101 Hz. In some embodiments, the complex waveform used to oscillate the bead comprises a combination of frequencies that are a predetermined multiple of prime frequencies, such as a set of frequencies of from 300 to 15700 Hz that are a predetermined multiple of prime frequencies. In some embodiments, the frequencies in the combination of frequencies are offset in phase. Use of a complex waveform composed of a combination of frequencies with distinct harmonics to oscillate the bead reduces Oscillating the trapped bead relative to the sample preferably does not exceed a linear range of viscoelasticity of the biological material. In some embodiments, oscillating the trapped bead relative to the sample comprises oscillations of no more than 200 nm.

In some embodiments, oscillating the bead relative to the sample comprises oscillating the trap beam using an acousto-optic deflector (AOD) when the sample remains stationary. In other embodiments, oscillating the bead relative to the sample comprises oscillating a nanopositioning stage (such as a piezo stage) holding the sample when the trap beam remains stationary.

Several embodiments comprise calculating a change in volts per nm of bead displacement for a position sensing detector (PSD), such as a quadrant photodiode (QPD), that detects the position of the detection beam downstream of the optical trap bead. In some embodiments, calculating the change in volts per nanometer of bead displacement for the PSD comprises stepping the biological material through the detection beam using a nanopositioning stage when the optical trap is not applied to the bead, and detecting the position of the detection beam downstream of the bead using the PSD. In other embodiments, calculating the change in volts per nanometer of bead displacement for the PSD comprises oscillating the detection beam when the optical trap is applied to the bead; and sensing the position of the detection beam downstream of the bead using the PSD.

In some embodiments, the disclosed method of assaying viscoelastic properties of a sample can be used to assay the viscoelastic properties of extracellular remodeling during development and cancer metastasis, keloid scar formation during wound healing, repair and regeneration of injured collagenous tissues such as tendon and cartilage, skin stiffening or softening, scar formation as scar stiffen or soften due to treatment, collagen fibrils and networks in vitro; and/or in vivo mechanical mammography.

The foregoing and other features and advantages of this disclosure will become more apparent from the following detailed description of several embodiments which proceeds with reference to the accompanying figures.

BRIEF DESCRIPTION OF THE FIGURES

FIGS. 5A-5D are a set of graphs showing that active optical trapping microrheology in matrigel and zebrafish resolves viscoelastic properties with high spatial resolution over a wide range of frequencies. An optical trap was used to perform multiplexed rheology measurements spanning frequencies from 3 to 15700 Hz in (5A) Matrigel (n>15), (5B) HA (n>15), and zebrafish (5C) brain (n>5) and (5D) tail (n>5). The trap-induced displacements of beads of diameter 1 mm were converted to storage (elastic) and loss (viscous) moduli using four different calibrations: with individual calibrations of the stiffness and volts-to-nanometers of each bead in situ (4); averaged stiffness over all beads measured (3); the average stiffness of the same beads calibrated in water using the power spectrum method (2); and the average volts-to-nanometers conversion for the QPDs calibrated in water (1). These comparisons demonstrate the improved accuracy of our technique. In addition, the right-most panels show high frequency linear fits to the data, where in 5A) the linear fits are all better than R2 of 0.98, and the lines' slopes are all significantly different ($p<0.01$), in 5B) HA, the linear fits are >0.98 for the loss moduli, and 0.92 for the storage moduli, with the lines' slopes again all significantly different ($p<0.01$). In (5C-5D), a similar comparison for data obtained in the tail (5C) and brain (5D) in the zebrafish is shown. Graphs depict averages over bead measurements, with the mean and (symbols) ♭/% standard error of the mean. For each sub figure, right panel shows the linear regression fits with >0.98 R2 in the loss modulus (bottom), and >0.93 in the storage (top). The lines' slopes were once again significantly different to a ($p<0.01$). Comparison of different calibration methods over all frequencies in all samples are also significantly different, as determined by the non-parametric Friedman test with $p<0.0001$.

FIG. 10A shows graphs of individual frequency sweeps, while FIG. 10B shows graphs of multiplexed frequency assays. The data shown in the FIG. 10A required 20 minutes per bead, while data shown in FIG. 10B was acquired in 40 seconds.

FIG. 11A shows graphs of individual frequency sweeps, while FIG. 11B shows graphs of multiplexed frequency assays. The data displayed in FIG. 11A required 20 minutes per bead, while data shown in FIG. 11B was acquired in 40 seconds.

FIGS. 13A-13C show a set of diagrams illustrating calibration for active microrheology in vivo. (13A) Determining micromechanical properties of interest can include calibration of the optical trap stiffness, K, and the positional sensitivity β (the V-nm conversion factor) of the detection system used to measure probe displacements. (13B) Because probes lie in different positions along the beam axis and in regions with different optical properties, measurements in vivo (such as in the depicted zebrafish embryo) require that both of these calibrations be conducted for every probe measured in the sample. In some regions, probes may be free to fluctuate in position because they are not tightly confined (e.g. in the viscous yolk), or are subject to flow (as in perivasculature). (13C) Two methods used to calibrate β are (1) the thermal power spectral density (PSD) method and (2) the piezo stage stepping method. In the PSD method, the probe is trapped and allowed to fluctuate due to thermal motion while voltage on the detector is recorded. Fluctuations in voltage are related by β to position fluctuations predicted by a fluctuation-dissipation model assuming probe radius and the drag coefficient, which is unknown. In the piezo stage stepping method, the probe is stepped through the detection beam as the stage is moved through known distances, while the voltage on the detector is recorded. This works well unless the probe and stage motions are not in tandem. FIG. 13C (3) To calibrate under such conditions, a detection beam steering method in which the trap is used to hold the probe stationary while the detection beam is scanned across the probe and the measured voltage is used to find β.

FIGS. 15A-15D illustrate methods for calibrating the V-nm conversion factor β. In the piezo stage stepping method, QPD voltage is recorded while the stage is stepped through the detection beam in defined steps (such as 12 nm steps) by moving the sample stage via piezo controller. (15A) In viscoelastic solids, the probe moves with the sample stage, so the recorded voltage correctly corresponds to the linear response of the detector to the interference pattern in the back focal plane of the condenser caused by the probe. Linear regression is used to get β from the voltage and position data. (15B) In liquid or liquid-like samples, the probe may move freely, and is not constrained to move in tandem with the stage, so the signal cannot be used to find the positional sensitivity. (15C and 15D) In the detection beam steering method, the probe is first trapped and held stationary. The detection beam is then steered using an acousto-optic deflector, oscillating across the probe center with an amplitude of ~55 nm and frequency of 1 kHz while the QPD voltage signal is recorded. To calculate β, the signal is Fourier transformed to find the voltage at the drive frequency.

DETAILED DESCRIPTION

Figure 1:
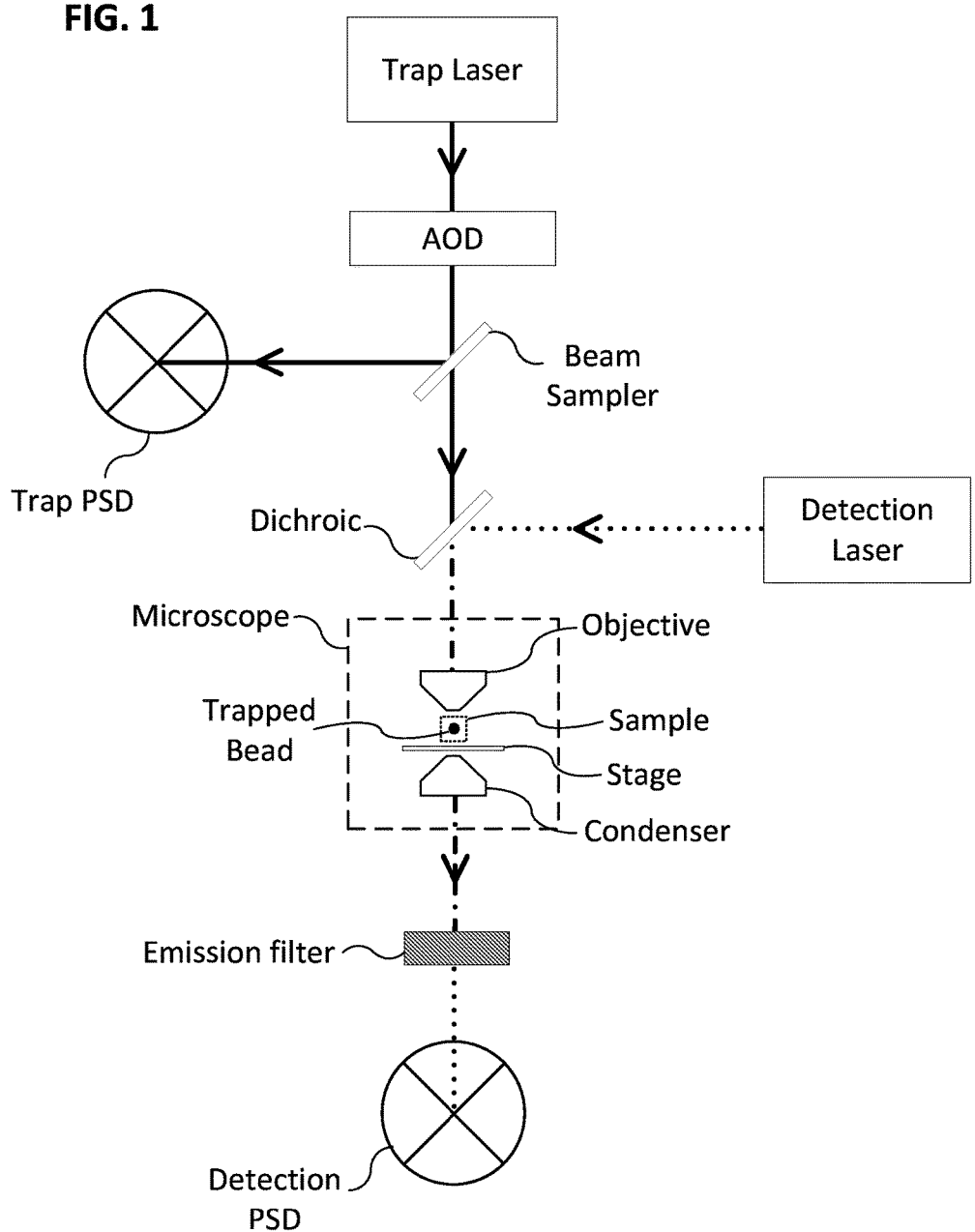
FIG. 1 is a schematic diagram illustrating aspects of an embodiment of an optical trap system for use with the disclosed methods.

The methods and systems disclosed herein involve the use of an optical trap to evaluate the viscoelastic properties of a sample, such as a biological material. In optical trap-based microrheology, small refractive probes are embedded in a sample to serve as local microenvironment sensors. An optical trap is applied to the embedded probe. Once trapped, the bead undergoes spring-like oscillations if perturbed by an applied force, where the displacement amplitude is related to the perturbing force by the trap stiffness. Accurate deduction of material characteristics by measurement of bead displacement requires that the trap stiffness is known. For non-complex materials, the trap stiffness can be estimated prior to an experiment by calibration in an appropriate material that is assumed to have the same refractive index as the sample. However, this approach is inapplicable to complex materials (such as in vivo and ex vivo samples), as tissues are optically heterogeneous and the refractive indices are unknown a priori.

To address issues associated with optical trap-based microrheology of complex materials, such as in vivo and ex vivo materials, modified optical trap-based microrheology systems and methods are provided. Using the disclosed systems and methods, it is possible, for the first time, to interrogate the viscoelastic properties of in vivo and ex vivo tissue using optical trap-based microrheology. This is a particularly surprising result, given that prior teachings posited that such measurements were not possible (see, for example, Tassieri, "Linear microrheology with optical tweezers of living cells 'is not an option'!," *Soft Matter*, 11:5792-5798, 2015).

An optical trap is a highly focused laser beam that provides an attractive or repulsive force to hold and/or move an optical trap bead having a dielectric charge in physical space. The laser beam is typically focused on the particle by sending it through a microscope objective. The narrowest part of the focused beam (the beam waist) has a strong electric field gradient. The dielectric optical trap bead is attracted to the strongest electric field on the gradient, which occurs at the beam waist. The optical trap bead is "trapped" when it is held in position by the force of the laser beam at the beam waist. "Applying an optical trap" refers to directing a laser beam to an optical trap bead under conditions such that the optical trap bead is held in position at the beam waist by electric field gradient of the focused beam. Once trapped, the optical trap bead can be manipulated in physical space by moving the trap beam relative to the sample containing the optical trap bead. Preferably, the optical trap can be operated in such a way that the dielectric particle does not move beyond the linear range of viscoelastic deformation of the local environment surrounding the bead.

Using the novel optical trapping procedures described herein, significant improvements in spatial resolution and tissue depth have been obtained, in particular for examining clinically relevant samples such as a biological material. As used herein, a biological material is a natural or synthetic material containing cells or containing the products of cells (such as the extracellular matrix). In some embodiments, the biological material can be a tissue from a subject. A subject can be, for example, any vertebrate animal, such as humans, non-human primates, pigs, sheep, cows, rodents, zebrafish, and the like. In two non-limiting examples, a subject is a human subject or a murine subject. In some embodiments, the biological material can be the skin of a mammal (such as a rabbit, a rat, a mouse, or human). In some embodiments, the biological material can be a biological sample obtained from a subject. Biological samples include all clinical samples useful for detection of disease or infection (for example, cancer) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In some embodiments, the biological sample is a tumor sample, such as all or a portion of a tumor and its microenvironment.

The sample contains one or more embedded optical trap beads that serve as a local sensors. As used herein, an optical trap bead is a dielectric particle that can be manipulated using an optical trap. In some embodiments, the optical trap bead can be a fluorescent dielectric bead having a diameter of between 0.1 and 10 µM (such as 1 µM). When applied to a sample for detecting and/or manipulation using an optical trap, the optical trap bead is preferentially monodispersed in the sample, for example, the optical trap bead does not aggregate in the sample. In some embodiments, the optical trap bead can be injected into a sample (such as a tumor sample) prior to performance of the methods as described herein. In some embodiments, the optical trap bead can be a fluorescent bead. In some embodiments, the optical trap bead can have an altered surface chemistry to target the bead as needed in a material of interest. For example, the optical trap bead can have a surface modification that targets the bead via ligand/receptor interaction to a particular cell type in a subject. In some embodiments, the optical trap bead can be linked to a binding moiety that specificity binds to a tumor associated antigen to target the bead to a particular tumor.

In some embodiments, the disclosed systems and methods can assay viscoelastic properties of a sample, such as a biological material at a penetration depth of up to 1000 µM in the sample, such as up to 500 µM, up to 400 µM, up to 300 µM, up to 200 µM, up to 100 µM, from 100-500 µM, from 100-1000 µM, from 200-1000 µM, from 200-500 µM, or from 300-700 µM.

Compared to magnetic bead-based microrheology, the disclosed systems and methods provide a localized, precise application of force. Compared to passive, thermally driven-based microrheology, the disclosed systems and methods have greater dynamic range, and can probe outside the thermal energy range, measuring non-linear effects at different length and energy scales. The viscoelastic measurements obtained using the disclosed systems and methods have a surprisingly high contrast-to-noise ratio compared to prior methods of obtaining viscoelastic measurements for complex materials, such as biological materials. The increased contrast-to-noise ratio allows for more sensitive detection of changes in viscoelastic properties across biological materials than what was possible using prior methods. For example, using the disclosed optical trapping systems and methods, the first description of live vertebrate microrheology and tumor sample microrheology was obtained and is provided herein. Thus, the disclosed systems and methods can be used to measure the microrheology of a wide variety of complex materials (such as biological materials), from 3D tissue culture models to tissue in or from living zebrafish to mammals, such as mice and humans.

FIG. 1 depicts aspects of an optical trap system for use with the disclosed methods. The system includes a trap laser and a detection laser. The trap laser produces a trap beam (solid line) that can be directed to an optical trap bead in a sample to apply an optical trap to the bead. The detection laser produces a detection beam (dotted line) that can be directed to the optical trap bead in the sample to detect movement of the bead relative to the sample.

As used herein, laser beam or beam refers to electromagnetic radiation at wavelengths of between about 100 nm and 10 µm, and typically between about 500 nm and 2 µm. Examples based on available laser diode sources generally are associated with wavelengths of between about 800 nm and 1700 nm. The trap and detection lasers produce beams of appropriate wavelengths so that the beams can be aligned and separated as needed for application of an optical trap of a bead and detection of bead displacement. In a non-limiting embodiment, the trap laser can be a 1064 nm diode laser, and the detection laser can be a 975 nm diode laser. Optical beams and optical elements are described in some examples with respect to one or more axes. Typically, an axis includes one or more straight line segments along which an optical beam propagates or along which one or more optical elements are situated. Such axes can be bent or folded with reflective surfaces, so that axes need not be single straight line segments.

Typical laser diodes have emission regions having non-circular cross-sections. An emission region of a laser diode can be associated with a slow axis that is directed along a longest dimension of the emission region and a fast axis that is directed along a shortest dimension of the emission region. Along the slow axis, an emitted beam tends to have a smaller angular divergence than the angular divergence along the fast axis. In addition, the slow axis tends to be associated with beam propagation in more transverse modes than beam propagation in the fast axis so that a beam parameter product (corresponding to a product of an angular divergence and a beam dimension) measured along the slow axis is larger than that measured along the fast axis. Beam divergences and diameters along the slow axis, the fast axis, or both can be adjusted with one or more lenses, prisms, or mirrors to provide selected beam characteristics.

Continuing with the embodiment depicted in FIG. 1, the light path of the trap laser is directed through an Acousto-Optic Deflector (AOD), which can be used to oscillate the trap beam to oscillate the trapped bead in the sample. The light path of the trap laser then continues to a beam sampler which is used to separate a small percentage of the beam, which is directed to a PSD (such as a QPD), to determine the oscillation of the trap laser. The sum, left-right difference, and top-bottom difference channel voltage readouts sensed by the trap PSD can be obtained by analog input channels of a data acquisition (DAQ) card in operable communication with the trap PSD.

The light paths of the trap beam and the detection beam are then directed to a dichroic mirror, which is used to align the paths of the two beams and direct the aligned beams (illustrated using a line with dashes and dots) towards the optical trap microscope.

In the illustrated embodiment, the microscope comprises an objective, a stage holding the sample with the embedded optical trap bead, and a condenser. In some embodiments, the objective can be a water immersion objective with a high numerical aperture, such as about 1.2. In some embodiments, the condenser can be a water immersion condenser. In several embodiments, the microscope stage can be a motorized stage for controlling movement in X, Y, and Z dimensions, such as a nanopositioning stage. The stage is configured for holding the sample, such as a biological material. The microscope can include any additional standard components that are useful for optical trap-based microrheology methods, such as a CCD camera and corresponding lamp for assistance in positioning a bead in the focal plane of the microscope objective.

As shown in FIG. 1, the aligned trap and detection beams pass through the microscope objective and are directed to the sample containing the optical trap bead before being collected by the condenser. The trap and detection beams are focused by the objective on the optical trap bead in the sample mounted on the stage of the microscope. Typically, the trap beam has a width that slightly overfills back aperture of the microscope objective, whereas the detection beam has a width that is smaller than the trap beam's width, and does not fill the back aperture of the microscope objective.

The trap beam and the detection beam are collected by the condenser. The light path from the condenser then passes through an emission filter that allows passage of the detection beam, but not the trap beam. In an alternative embodiment, the light path from the condenser can pass through a dichroic mirror that separates the trap and detection beams. The light path of the detection beam continues to a PSD (such as a QPD), to determine the position of the detection beam. The sum, left-right difference, and top-bottom difference channel voltage readouts sensed by the detection PSD are obtained by analog input channels of the DAQ card.

Figure 2:
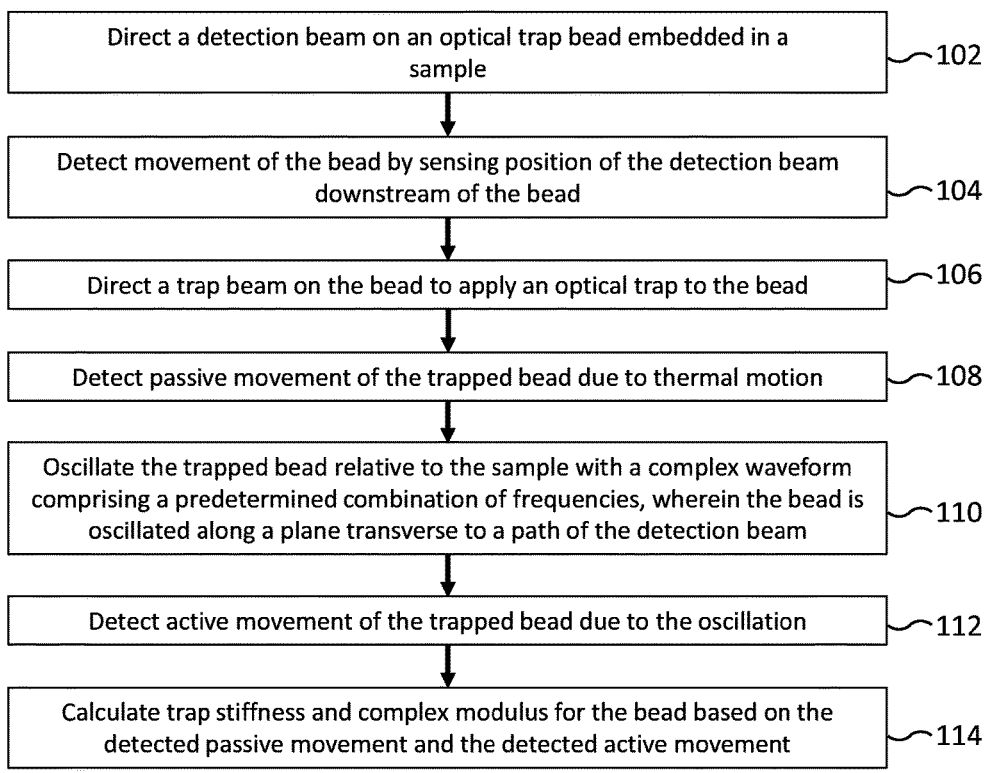
FIG. 2 is a flow chart illustrating an exemplary embodiment of a process for assaying viscoelastic properties of a sample.

Time-correlated trap and probe QPD signals are recorded on the DAQ, which also controls radio frequency signals that drive the AOD. FIG. 2 depicts an embodiment of a disclosed method for assaying viscoelastic properties of a sample, such as a biological sample, using an optical trap. Using this method, it is possible for the first time to interrogate the viscoelastic properties of in vivo and ex vivo tissue samples using an optical trap.

When a laser beam focuses on a bead, refraction-induced changes in the momentum of light produce a harmonic potential within the laser's focal volume, trapping the bead in a force field such that it undergoes spring-like oscillations about the trap center if perturbed by an applied force, where the displacement amplitude of the bead $\Delta x$ is related to the perturbing force F by the trap stiffness k by $F=-k\Delta x$. Accordingly, accurate deduction of force F by direct measurement of bead displacements requires that trap stiffness k is known. In several embodiments, the disclosed methods of assaying viscoelastic properties of a sample, such as a biological sample, using an optical trap, provide superior procedures for calibrating the trap stiffness for a bead embedded in a sample.

Prior to performance of the disclosed methods, the optical trap system can be calibrated as needed using standard methods. For example, the optical trap system can be calibrated for alignment and functionality using a control sample containing embedded optical trap beads.

As shown in FIG. 2 at process block 102, the embodiment comprises directing a detection beam on an optical trap bead embedded in a sample, such as a biological material. The sample is typically mounted on a stage on a microscope included in an optical trap system, such as described herein. Directing the detection beam on the optical trap bead can comprise directing a detection beam of appropriate wavelength through a microscope objective to be focused on an optical trap bead embedded in a sample.

As shown in process step 104, movement of the bead is detected by sensing a position of the detection beam downstream of the bead. One way to measure probe displacements in optical trap systems is by back focal plane interferometry (see, e.g., Denk and Webb, *AppL Opt.*, 29(16) 2382-2391 (1990); and Allersma et al., *Biophys. J.*, 74(2) 1074-1085 (1998), each of which is incorporated by reference herein). When a probe of diameter d is trapped at the center of the beam waist of a laser with wavelength λ focused by an objective in its image plane, some light undergoes scattering due to light-probe interactions and (in the dipole limit d<λ) produces spherical waves. This scattered light slightly diverges from the fraction of light that does not undergo scattering. Thus, shifts in relative phase between these two wavefronts give rise to a pattern of constructive and destructive interference. A condenser collects this light, and is placed such that the image planes of the field diaphragm iris and the objective are conjugate and image into each other (forming a Keplerian telescope). Behind the condenser, a dichroic mirror or emission filter separates the detection beam (but not the trap beam or lamp light) onto a detection lens that is positioned to relay the image at the back focal plane of the condenser onto a PSD, such as a QPD. In this configuration, displacements of the probe cause rotation of the detection beam in the image plane and corresponding translations of the beam at both the back-aperture of the condenser and on the detection QPD. The interference pattern is mapped onto the QPD; so lateral displacements of the probe relative to the detection beam in the imaged plane result in changes in voltage. The voltage response $\Delta S_x$ is linearly related to probe translations for small displacements ($\Delta x \pm \sim 150$ nm from the probe center). Thus, calibrating the position detection sensitivity consists in finding the V-nm relation $\Delta x = \beta \cdot \Delta S_x$ in the linear response regime.

The PSD preferably can be calibrated for each optical trap bead to determine a change in volts per nm of bead displacement (V-nm conversion) detected by the PSD for that particular bead. In several embodiments, the change in volts per nanometer of bead displacement, $\beta$, is calculated for the PSD (such as a QPD) that senses movement of the detection beam downstream of the bead. Exemplary methods for determining $\beta$ for particular bead embedded in a sample are provided in the Examples below. In some embodiments, this calibration step comprises, stepping the bead through the detection beam by moving the stage holding the sample in x and y dimensions (for example, 10 nm per step, 11 steps). This step is performed when the bead is not trapped by the trap beam. The PSD voltage can be recorded and normalized to the sum of the total voltage on the PSD for each dimension (x and y). A condenser collects scattered light from the bead and the conjugate image of the bead is mapped onto the back-focal plane and collected on the PSD. A line fit to the data is used to obtain a volt to nanometer conversion in both dimensions (x and y). Exemplary procedures for determining volt to nanometer calibrations for an optical trap bead are described in Examples 1 and 3. In some embodiments, a detection beam steering approach is utilized for determining $\beta$, as described in Example 3 below. The detection beam steering approach uses a weak detection beam to scan across the probe while it is confined in the optical trap for determining $\beta$ for a particular optical trap bead. The detection beam steering approach is particularly useful for determining $\beta$ when the bead of interest is either weakly attached to or freely moving through the sample microenvironment, such as in the perivascular microenvironment in the zebrafish trunk. The detection beam steering approach is also useful for calibrating $\beta$ for optical trap beads that are strongly attached or confined in a solid-like microenvironment, and the microenvironment may be non-linear, viscous, elastic or viscoelastic with unknown Brownian dynamics.

At process step 106, a trap beam is directed to the optical trap bead in the sample. Typically, a microscope objective is used to focus the trap beam on the bead. After passing through the microscope objective, the trap beam forms a beam waist, and the optical trap bead is attracted to the position of the beam waist by electric field gradient. Once "trapped," the movement of the bead due to passive (thermal) motion can be assayed by detecting the position of the detection beam downstream of the bead, for example, using the PSD. Additionally, the optical trap bead can be manipulated in physical space by moving the trap beam relative to the sample, and the movement of the bead due to this active motion can also be assayed by detecting the position of the detection beam downstream of the bead, for example, using the PSD.

As shown in FIG. 2 at process step 108, the passive movement of the bead due to thermal motion is detected. For this step, the optical trap is applied to the bead, and motion of the bead when the sample and the trap beam are held steady is assayed by detecting the position of the detection beam downstream of the bead. In some embodiments, the thermal power spectrum of the bead's passive thermal motion $P_U(\omega)$ can be recorded as:

$$P_U(\omega) = \langle |\tilde{x}_U(\omega)|^2 \rangle, \quad \text{equation (1)}$$

where $\tilde{x}_U$ is the Fourier transform of the undriven (passive) position data, and $\omega = 2\pi f$, where f is the frequency.

At process step 110, the trapped bead is oscillated relative to the sample and along a plane transverse to the path of the detection beam. In some embodiments, the bead can be oscillated relative to the sample by oscillating the trap beam using an acousto-optic deflector (AOD) when the sample remains stationary. In other embodiments, the bead can be oscillated relative to the sample by oscillating a nanopositioning stage (such as a piezo stage) holding the sample when the trap beam remains stationary.

The trap beam (or stage) can be oscillated with a complex waveform comprising a predetermined combination of frequencies. In some embodiments, the complex waveform used to oscillate the bead comprises a combination of frequencies (for example, from 10-50 frequencies, such as from 10-30 frequencies, from 10-20 frequencies, from 15-25 frequencies, or 10, 15, 20, 25, 30, 35, 40, 45, or 50 frequencies) that are selected to provide distinct harmonics and reduce cross talk, and to cover a frequency range that can provides sufficient data for determination of the trap stiffness. For example, the complex waveform used to oscillate the bead comprises a combination of prime frequencies (for example, from 10-50 prime frequencies, such as from 10-30 frequencies, from 10-20 prime frequencies, from 15-25 prime frequencies, or 10, 15, 20, 25, 30, 35, 40, 45, or 50 prime frequencies). In some embodiments, the complex waveform used to oscillate the bead comprises a combination of frequencies that are a predetermined multiple (such as 10×, 50×, 100×, or 200×) of prime frequencies that are selected to provide distinct harmonics and reduce cross talk, and to cover a frequency range that can provides sufficient data for determination of the trap stiffness. In some embodiments, the combination of frequencies can comprise or consist of frequencies (such as prime frequencies) of from 3 to 101 Hz, from 3 to 157 Hz, from 3 to 997 Hz, from 2 to 101 Hz, from 2 to 157 Hz, from 2 to 997 Hz, from 1 to 10 Hz, from 1 to 1000 Hz, from 1 to 10000 Hz, from 1 to 20000 Hz, from 100 to 1000 Hz, from 100 to 10000 Hz, from 100 to 20000 Hz, from 300 to 1000 Hz, from 300 to 10000 Hz, from 300 to 20000 Hz, from 1000 to 10000 Hz, or from 1000 to 20000 Hz, for example. In some embodiments, 2 sets of twenty multiplexed frequencies, ranging from 3-101 and 300 to 15700 Hz, can be obtained, and the high frequency data can be used to calibrate the trap (due to lower noise present at high frequencies in the power spectrum, trap calibration was much more accurate at the higher frequencies).

In some embodiments, to ensure that the amplitude of the resulting multiplexed waveform results in a maximum displacement of the probe that remains within the linear range of both the trap and detection beams, the component sines of the combination of frequencies in the complex waveform are given phase offsets. For example, the frequencies can be offset in phase by 0°, 45°, −45°, and −90°. The effect of the phase offsets is to reduce the stacking of the peaks of (especially the lower) frequencies so the bead does not exceed a linear range of viscoelasticity of the biological material. In some embodiments, oscillating the trapped bead relative to the sample comprises oscillations of no more than 200 nm from the bead's equilibrium position.

In some embodiments, oscillation amplitude per frequency and laser power can both be modified to alter the level of stress/strain applied to the sample. Laser powers can be varied between 10-500 mW (measured immediately before entry into the rear port of the microscope), as needed. In some embodiments, laser oscillation amplitudes can be varied between 1-100 nm to ensure the optical trap and trapped bead remain in the linear regime of detection beam and trapping laser.

In addition to multiplexed frequency measurement, measurements at single frequencies (1, 10, 100, 1000, 10000 Hz), with oscillation amplitudes of 1, 10, or 100 nm, and/or laser powers of 10, 50, 100 or 500 mW can be used.

In some embodiments, the trap beam (or sample stage) is first actively oscillated, followed by a passive phase in which the trap is held stationary at the bead's equilibrium position. In non-limiting embodiments, the measurements can be acquired with 1 s (½ s active, ½ s passive) pulses for a set number of seconds (such as 1, 2, 3, 4, 5, 6, 7, 8, 9, 10, 20, 30, or 60 seconds) at an appropriate acquisition rate such as 80 kHz, or 2-s pulses (1 s passive, 1 s active) for a set number of seconds (such as 1, 2, 3, 4, 5, 6, 7, 8, 9, 10, 20, 30, or 60 seconds) at an appropriate acquisition rate, such as 20 kHz. During the active pulse, the trap position is oscillated by a multiplexed waveform consisting of the sum of sines spanning a broad band of frequencies. After the trap is displaced according to the waveform, the probe motion is recorded with trap stationary during the passive pulse.

In some embodiments, the trap position is oscillated to drive bead displacement, and the active power spectrum $\tilde{R}_L(\omega)$ is recorded as:

$$\tilde{R}_L(\omega) = \frac{\tilde{x}_{dr}(\omega)}{-i\omega \tilde{x}_L(\omega)}, \quad \text{equation (2)}$$

where $\tilde{x}_{dr}(\omega)$ and $\tilde{x}_L(\omega)$ are Fourier transforms of the driven bead and trapping laser positions, respectively. Note that $\tilde{x}_{dr}(\omega)$ and $\tilde{x}_L(\omega)$ are complex, accounting for the relative phase of the trap and bead oscillations.

Based on the measurements of passive and active movement of the bead, the trap stiffness can be calculated, for example, using equation (3):

$$\kappa_\omega = \frac{\text{Re}\{\tilde{R}_L(\omega)\}}{P_U(\omega)}, \quad \text{equation (3)}$$

where Re indicates the real component and $k_\omega$ is the trap stiffness at $\omega$. The trap stiffness is typically constant over all oscillation frequencies as long at the bead is oscillated in a linear range of viscoelasticity of the sample. The friction relaxation spectrum can then be obtained with equation (4):

$$\tilde{\gamma}_D(\omega) + i\omega m = -\frac{\kappa_\omega}{i\omega}\left(\frac{1}{i\omega \tilde{R}_L(\omega)} + 1\right), \quad \text{equation (4)}$$

and the complex modulus can be derived from the relaxation spectrum for spherical probes of a known radius R by equation (5):

$$G^*(\omega) = \frac{i\omega \tilde{\gamma}_D(\omega)}{6\pi R}, \quad \text{equation (5)}$$

In some embodiments, the disclosed systems and methods can utilize automated programming, allowing the selection of multiple probe sites at once, to increase throughput. In addition, further automation (automated probe selection), and efficient selection of necessary experimental variables can be used to reduce assay time.

In some embodiments, the disclosed systems and methods can assay viscoelastic properties of a sample, such as a biological material, with a broad dynamic range of movement and force applied to an optical trap bead (such as from 1-10000 Hz, 1-10000 s Pa, and/or 1-200 nm), and can resolve changes in the local rheology on the order of 10 s of microns and 10 s of microseconds scale. By actively probing at a wide range of frequencies (1-20,000 Hz), amplitudes (1-200 nm) and trap powers (1-500 mW), it is possible to measure the properties of the sample microenvironment surrounding the trapped bead on different time, length, and force scales. The disclosed systems and methods can also be used to measure the local rheological anisotropy by oscillating in more than one dimension.

In some embodiments, the movement and force applied to an optical trap bead can have a frequency of from 1-20,000 Hz, such as from 1-20,000 Hz, from 10-20,000 Hz, from 100-20,000 Hz, from 1000-20,000 Hz, from 1-15,000 Hz, from 10-15,000 Hz, from 100-15,000 Hz, from 1000-15,000 Hz, from 1-10,000 Hz, from 10-10,000 Hz, from 100-10,000 Hz, or from 1000-10,000 Hz.

In some embodiments, the movement and force applied to an optical trap bead can have an optical trap force of from 1-10000 Pa, such as from 1-100 Pa, from 10-10000 Pa, from 100-10000 Pa, from 1000-10000 Pa, from 1-1000 Pa, from 10-1000 Pa, from 100-1000 Pa, from 1-5000 Pa, from 10-5000 Pa, from 100-5000 Pa, or from 1000-5000 Pa.

In some embodiments, the movement and force applied to an optical trap bead can have an amplitude of movement of from 1 to 200 nm, such as from 1-10 nm, from 1-100 nm, from 1-20 nm, from 1-50 nm, from 10-50 nm, or from 100-200, or from 50-200 nm.

In some embodiments, the force applied to an optical trap bead can be applied with a trap power of from 1-500 mW, such as from 1-100 mW, from 5-100 mW, from 10-100 mW, from 50-100 mW, from 5-500 mW, from 10-500 mW, from 50-500 mW, from 100-500 mW, or from 1-10 mW, or 1 mW, 10 mW, 50 mW, 100 mW, 200 mW, or 500 mW.

In cases where the assayed sample is optically transparent, for example 3D tissue cultures and in vivo tissues, a forward scattering optical trap system can be used. For samples that are not optically transparent, a backward scattering optical trap system can be used.

The disclosed methods and systems can also be used in the diagnosis and/or treatment of a particular condition or disease associated with tissue/cell remodeling, including tumor state. The disclosed methods and/or systems can be used to determine the effectiveness of a particular compound or treatment regimen for altering the viscoelastic properties of a sample, such as a tissue (for example skin or tumor tissue). For example, the present methods and systems can be utilized to determine the effectiveness of cosmetic products, such as the effectiveness of products for reducing wrinkles and scarring of skin. In some examples, the disclosed methods and systems are used to evaluate wound healing, such as to determine the effectiveness of a treatment for wound healing, including, but not limited to, wound healing in a diabetic patient.

In some embodiments, the disclosed systems and methods can be used to interrogate the viscoelastic properties of a tumor and/or the tumor microenvironment. During metastasis, tumor cells encounter new microenvironments. First, they adhere and remodel the host organ to proliferate and form a new neoplasm, or a new tumor organ. Tumor cells receive both chemical and physical cues from the surrounding stromal cells and the extracellular matrix within this dynamic milieu. Preliminary studies have indicated that physical properties involving stiffness, dimension and topography strongly influence cell fate and malignancy (Gauvin and Khademhosseini (2011) *Acs Nano* 5(6): 4258-4264; Kumar and Weaver (2009) *Cancer Metast Rev* 28(1-2): 113-127; Yang et al., (2005) *Biomaterials* 26(15): 2603-2610). In particular, the physical properties of the local (microscale) environment, such as the forces that cells experience, influence gene expression, cell signaling, and motility (Wang et al., (2009) *Nat Rev Mol Cell Bio* 10(1): 75-82). These data indicate that microscale mechanical heterogeneities are major factors in cancer outcome.

In several embodiments, the disclosed systems and methods can be used to interrogate the rheological properties of tumors and/or the tumor microenvironment. For example, such assays can be performed before any after application of a test agent to determine if it alters the tumor or the tumor microenvironment. A tumor is an abnormal growth of tissue or cells that results from excessive cell division. A tumor that does not metastasize is referred to as "benign." A tumor that invades the surrounding tissue or can metastasize (or both) is referred to as "malignant." The tumor microenvironment is the cellular environment in which a tumor exists, including surrounding blood vessels, immune cells, fibroblasts, signaling molecules, and the extracellular matrix (ECM), including stromal cells. Tumors can influence the microenvironment by releasing extracellular signals, promoting pathological angiogenesis and inducing peripheral immune tolerance, while the immune cells in the microenvironment can affect the growth and evolution of cancerous cells. In some embodiments, the disclosed systems and methods can be used to assay the viscoelastic properties of mechanical fibrosis in clinically relevant samples, such as ductal carcinomas with fibrotic focus, which are more likely to recur and metastasize.

Non-limiting examples of tumors and/or tumor microenvironments that can be assayed include the following tumor types as well as their microenvironment: sarcomas (connective tissue cancer) and carcinomas (epithelial cell cancer), including fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colorectal carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest," "best," "minimum," or the like. It will be appreciated that such descriptions are intended to indicate that a selection among many used functional alternatives can be made, and such selections need not be better, smaller, or otherwise preferable to other selections.

EXAMPLES

The following example is provided to illustrate particular features of certain embodiments, but the scope of the claims should not be limited to those features exemplified.

Example 1

In Situ Calibrated Mechanical Properties of Tissue Microenvironment In Vivo

The example provides an active microrheology optical trapping method for analysis of the viscoelastic properties of heterogeneous biological materials, such as in vivo samples. In the disclosed method, optical trap beads are calibrated in situ to obtain trap stiffness to quantify local applied forces. Applicable to multiple sample types, including thick tissue, this method allows quantitation of mechanical heterogeneities with micrometer spatial resolution at penetration depths up to 500 mm, such as in living zebrafish. Microscale differential stresses and strains were applied over a broad range of frequencies to measure the mechanical response of distinct organs to reveal the frequency dependent viscoelasticity on time, length, and force scales relevant to protein-protein interactions, cytoskeletal remodeling, molecular motor activity, in addition to slower processes such as 3D cell motility, cell proliferation and the establishment of multicellular structures.

Materials and Methods

Sample Preparation—Microrheology

ECM Hydrogels.

Matrigel (Corning (#354230, Lot #3032578)) and Hyaluronan (ESI BIO (Hystem #GS311)) were stored at 4° C. until use. Gels were polymerized as previously described (Blehm, et al., Biomaterials 56 (2015) 129e139; Tanner et al., PNAS, 109 (6) (2012) 1973e1978). Briefly, carboxylate modified red fluorescent beads (Life Technologies Fluorospheres, F8887) ~1 mm in diameter were first sonicated for 45 min immediately before use. Fluorescence excitation of the beads was 546 nm. These monodisperse beads were then uniformly mixed into either the liquid Matrigel or Hyaluronan at a density of 5×108 beads/mL chilled on ice. 450 ml of this bead-ECM mixture was directly pipetted into a Willco Well dish (WillCo Wells, GWSB5040), and allowed to polymerize in an incubator at 37° C. for 90 min. Cell media was then added to the well, and the dish was returned to the incubator until used. The measurements are performed in an aqueous environment at room temperature.

Zebrafish.

The transgenic zebrafish line Tg(kdrl:GFP)la116), which stably expresses EGFP in the vasculature, was used. Zebrafish were maintained at 28.5° C. on a 14-h light/10-h dark cycle according to standard procedures. Embryos were obtained from natural spawning and raised at 28.5° C. and maintained in egg water containing 0.6 g sea salt per liter of DI water. Embryos were injected at the single cell stage with 2 nL of bead/sterile PBS solution of 5×108 beads/mL of monodisperse carboxylate-modified red fluorescent beads. Between 10 and 16 h post fertilization (hpf), embryos were transferred to eggwater supplemented with phenylthiourea (PTU, Sigma P5272), suspended at 7.5% w/v in DMSO, at 1 part in 4500 to inhibit melanin formation and increase optical transparency. Embryos were then returned to the incubator at 28.5° C. and checked for normal development and widely dispersed beads daily using fluorescence microscopy. Mechanical characterization was performed 72 h post fertilization (72 hpf). Zebrafish embryos were anesthetized using 0.4% buffered tricaine, then embedded in a lateral orientation in 1% low melting point agarose (NuSieve GTG agarose, Lonza), and allowed to polymerize on a 50 mm glass bottom dish with cover glass no. 1.5 thickness. Egg water supplemented with tricaine was added to the agarose hydrogel for the entire time of data acquisition and used as the immersion medium. The maximum time of data acquisition on each embryo did not exceed 4 h. Fish were fixed in 4% paraformaldehyde solution for 2 h and then prepared for histological staining Briefly, fish were embedded in Optimal Cutting Temperature compound (OCT) prior to frozen sectioning on a microtome-cryostat. Serial sections 8 microns thick were labeled for specific stains as delineated by Masson trichrome, modified Movat and Haematoxylin and eosin. Briefly, the slides were hydrated and then stained with hematoxylin and eosin. They were then dehydrated and cleared and cover slipped, resulting in nuclei stained blue and cytoplasm pink. For *M. trichrome*, the slides were hydrated, then mordant in bouin to stain slides in Weigert hematoxylin followed by biebrich scarlet/Acid fuchsin combo. The slides were then placed in a combination of phosphomolybdic and phosphotungstic acid. Finally, they were stained with aniline blue and then hydrated and cleared. The slides were mounted with permount. Collagen stains blue and muscle red. For Movat after hydration, slides were stained with verhoeffs hematoxylin, followed by treatment with 2% ferric chloride. The slides were then placed in 5% hypo solution and stained in 1% alcian blue, then with a combination of crocein scarlet and acid fuchsin. They were then rinsed in 0.5% acetic acid and finally stained with alcoholic saffron solution. Nuclei stain black, cytoplasm red, collagen yellow, elastic fibers black and muscles stain red.

Optical Trap.

Figure 3:
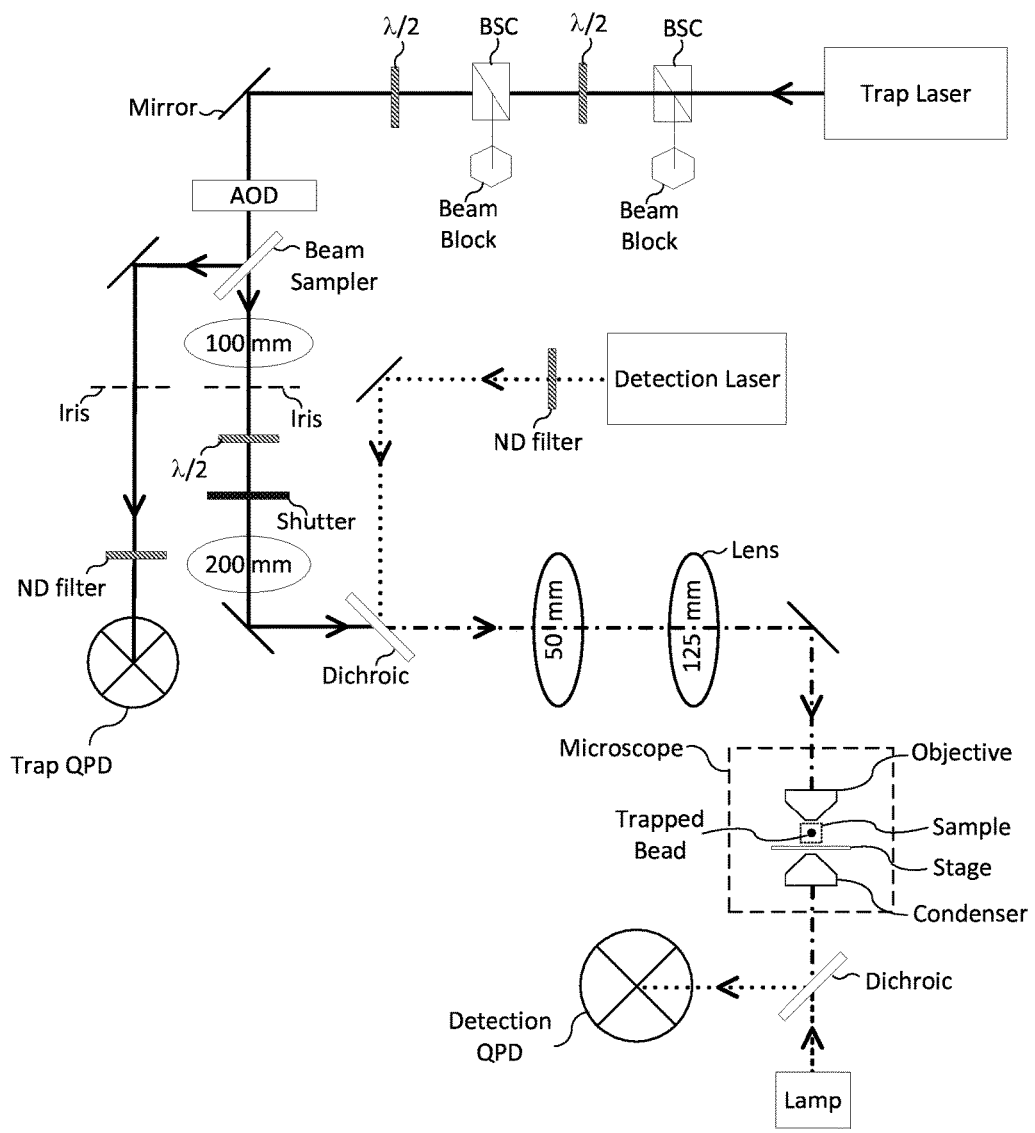
FIG. 3 is a schematic diagram illustrating aspects of an embodiment of an optical trap system for use with the disclosed methods.

A simplified schematic of the instrument is shown in FIG. 3. The optical trap is comprised of two lasers, one that traps and one that detects. The light path of the trapping laser originates from non-polarized light emitted by an IPG Photonics 1064 nm laser (#YLR20-1064-Y11). This beam is then linearly polarized by placing a polarizing beam splitter cube (Thorlabs PBS23) into the light path. Beam power is either manually controlled by adjusting a half-wave plate (WPH05M-1064) or controlled by changing the input voltage of the power supply of the trap laser. For the latter, manipulation is achieved using an analog channel of a DAQ card (#PCIe-5871R FPGA DAQ, National Instruments), or manually on the touchscreen of the power supply. This adjusted beam is then directed through another beam splitter cube. Trap steering at the sample plane is achieved by using a 2D Acousto-Optic Deflector (AOD) from IntraAction (DTD274HD6), which is conjugated to the back focal plane. The AOD is driven by radio frequency (RF) generating cards (Analog Devices #AD9854/PCBZ), which are controlled by the digital outputs of the data acquisition (DAQ) card (#PCIe-5871R FPGA DAQ, National Instruments). A second half-wave plate is used to direct the correctly polarized beam into the AOD. The AOD mount (New Focus 9081, Newport) is used to adjust the beam's entrance angle to ensure maximal diffraction into the doubly diffracted first-order beams. This customized adjustable AOD mount required machining a coupling plate to attach the AOD. An iris is used to isolate the doubly diffracted first-order diffracted beam. This beam is then directed into the objective with two lens telescopes (100 mm and 200 mm, and 50 mm and 125 mm, LA1509-C, AC508200-B, LA1131-C, LA1384-C respectively, Thorlabs). A third half-wave plate in the beam path allows for polarization adjustments to the beam before it enters the microscope. A beam pick (BSF10-C, Thorlabs) is used to separate ~1 percent of the beam, which was attenuated with a ND Filter (NENIR210B, Thorlabs), and directed to the trap QPD (QP154-Q-HVSD, First Sensor), to determine the oscillation phase of the trap laser. An iris is once again used to isolate only the doubly diffracted first-order diffracted beam.

Spatial distortion in the beam profile is introduced when the trapping beam is diffracted by the AOD. The detection beam removes this noise. The detection laser was a 975 nm Lumics diode (#LU0975M00-1002F10D) cased in a Thorlabs mount (LM1452, TED200C, DC210C). This laser can only be operated at a very high power (>10 mW). Hence, the power was attenuated by first passing the beam through a neutral density (ND) filter (NENIR220B, Thorlabs) reducing the power to <1 mW. Alignment of the attenuated detection beam with the trapping laser beam was achieved by manipulation of a broadband dielectric mirror (BB1EO3IR, Thorlabs) and a dichroic mirror (T1020LPXR, Chroma). The trapping beam enters the objective (MRDO7602 CFI-PLAN-APO VC60XA WI 1.2NA, Nikon), slightly overfilling its back aperture (the detection beam is much smaller). Both beams are sent into the objective by reflection off a filter cube (ZT1064rdc-2p dichroic, Chroma). The two beams are then collected by a water condenser (WI 0.9NA, Nikon), before being decoupled from the microscope light path by a dichroic mirror (ZT1064RDC-2P, Chroma) that was attached to the microscope using custom machining The trapping beam is then filtered using an emission filter (ET980/20X, Chroma). A First Sensor Quadrant PhotoDiode (QPD) (QP154-Q-HVSD) is used to determine the position of the detection beam and the sum, left-right difference, and top-bottom difference channel voltage readouts are obtained by analog input channels of the DAQ card.

The microscope stage is controlled by both a motorized stage (X-Y-Z axes) (Prior #77011201) and a piezo stage (X-Y-Z axes) (Mad City Labs #77046501). Images were acquired with an ANDOR Ixon real gain camera (DU-897E-C50-#BV). Bright field illumination was achieved using a Prior LED light source (LDB101-NI). The supplemental mirrors and irises shown in the schematic not specifically detailed above were all obtained from Thorlabs (part numbers: BB1-E03IR, BB2-E03IR, ID25). The shutter is from Uniblitz (VS1452Z0R3) and the base microscope is a Nikon Eclipse Ti-U. Data acquisition and laser control were achieved using custom Labview programs.

Power Supply and Other Electronics.

Electronics used in the setup were driven by Acopian power supplies: A50MT100 (QPD bias voltage), TD15-40 (QPD power), A24H1500 (amplifier power), and A3.3NT350 (RF card power). The RF cards for the AOD had onboard 60 MHz crystal oscillators (Anodyne Components, ZKG10A1N-60.000M) multiplied 5× onboard to give a reference clock of 300 MHz. The RF signal was then amplified (Minicircuits, ZHL-1-2 W-S♭) and DC blocked (Minicircuits, BLK-89-S♭). All RF cable connections were comprised of triply shielded cables (Minicircuits, cb1-10FT-SMSM♭) to reduce noise. All electronics were powered by filtered AC that had been first passed through a Back-UPS Pro1000, and then an isobar ultra.

Microrheology

Calibration of Laser Alignment.

A optical trap built around a modified Nikon Eclipse TieU microscope base was used for all trapping measurements. Before each experiment, the trap was calibrated for alignment and functionality using a control sample of carboxylated beads in PBS at a concentration of 107 beads per mL. Briefly, the calibration involves trapping a bead, which is then oscillated using the AOD at magnitudes that can be easily observed on the CCD camera (typically equivalent to 500 nm). The trap's oscillation is detected on the trap QPD, and then the detection laser's response is verified on the detection QPD. Maximum response to oscillations in both dimensions (x and y), while ensuring oscillation in either dimension is also decoupled from the other dimension, is found by adjusting the detection laser mirror and dichroic mirror. This signal is then centered in the middle of the range where its response is optimal. The detection QPD is then adjusted such that the detection beam is centrally located in both x and y. Once this is accomplished, the trap is calibrated in water using the power spectrum method (see, e.g., Visscher et al., Nature 400 (6740) (1999) 184e189, which is incorporated by reference herein in its entirety) and then calibrated using the active-passive method described herein. Finally, the bead position on the CCD is determined by centroid-fitting an image of the bead on the camera, and this position is used as the trap position in the trap-centering algorithm.

Data Acquisition.

Figure 9A:
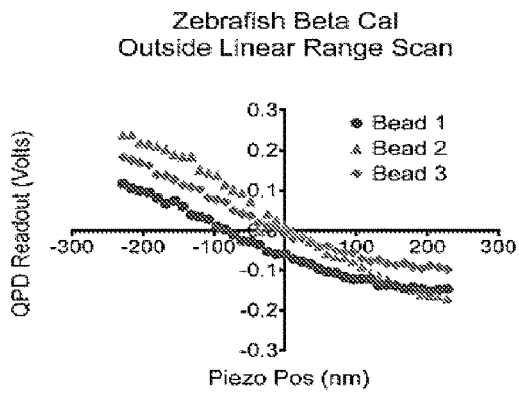
FIGS. 9A and 9B are a set of graphs showing results of QPD voltage to nm bead displacement calibration. (9A) Measurements across the entire range of piezo stage positions, showing the tapering/nonlinearities at the edges of the range. (9B) Measurements across a linear range.
Figure 9B:
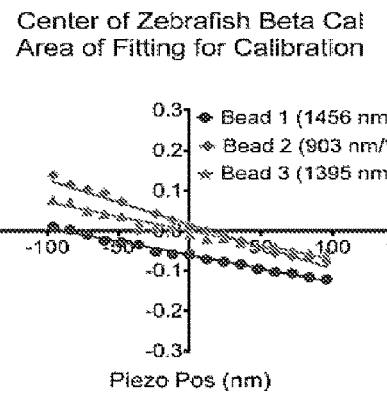

Samples are loaded on the microscope stage. Typically, an image of 512×512 square pixels is recorded by the CCD camera, and then beads that are in focus at a given plane are manually selected. The software records the positions of each of these beads and the active oscillation is performed systematically, where the data acquisition proceeds bead by bead. For each bead, an image of a subset of the original area encompassing 21×21 square pixels is acquired for each bead's position, and then the centroid is estimated to determine the bead's center. The trap laser is then centered to that bead's location by the piezo stage. A 49-image z stack comprised of images 100 nm apart is acquired, and the center of the bead in the axial direction (z axis) is determined by detection of the maximum bead intensity. With the trap laser off, a volt to nanometer conversion calibration for each bead is calculated by stepping the piezo stage in X and Y (10 nm per step, 11 steps) through the bead. The detection QPD's voltage is recorded and normalized to the sum of the total voltage on the QPD for each dimension (x and y). A high NA condenser collects all scattered light from the bead and the conjugate image of the bead is mapped onto the back-focal plane and collected on the QPD (Farré & Montes-usategui, 2010; Gittes & Schmidt, 1998; Grange, Husale, Güntherodt, & Hegner, 2002; June, Tripathy, Narayanareddy, Mattson-hoss, & Gross, 2014). A line fit to the data is used to obtain a volt to nanometer conversion in both dimensions (x and y). Example volt to nanometer calibrations performed in zebrafish are shown in FIG. 9. An additional check can be performed to ensure that this conversion is correct. For example, if the measurements are not linear where the R2 is <0.95, the entire dataset for that bead can be discarded. The volt to nanometer conversion is usually the major source of noise when calibrating the bead displacement for optically heterogeneous samples.

In Situ Calibration.

Figure 4A:
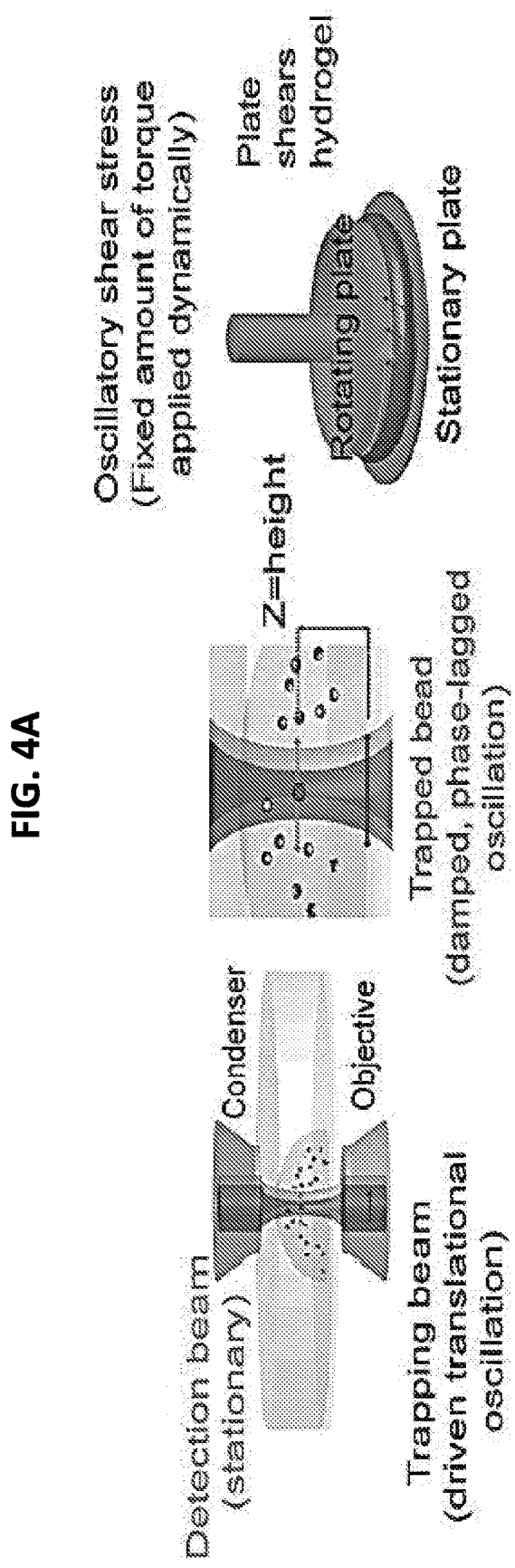
FIGS. 4A and 4B show a set of schematic diagrams and graphs illustrating bulk rheology and microrheology. (4A) Schematic of the method to obtain rheological parameters of materials using an optical trap. The optical trap is composed of a trapping laser (dark grey) and a detection laser (light grey). The trapping laser is used to actively modulate a single bead (middle panel) with high spatial resolution. In a bulk rheometer (right), sample material ~1 mm thick is sandwiched between rigid parallel plates, and rotational shear is applied at various amplitudes and frequencies. (4B) Microrheology measurements (left), enlarged at low frequencies (middle), and bulk rheology measurements at the low frequencies (right) in matrigel and HA (n=3 separate samples for each measurement).

In OT-based microrheology, small refractive probes are embedded in tissue to serve as local microenvironment sensors (FIG. 4A). When a laser beam focuses on a bead, refraction-induced changes in the momentum of light produce a harmonic potential within the laser's focal volume, trapping the bead in a force field such that it undergoes spring-like oscillations about the trap center if perturbed by an applied force, where the displacement amplitude $\Delta x$ is related by $F=-k\Delta x$ to the perturbing force F by the trap stiffness k. In passive microrheology, mechanical properties of the bead's local microenvironment are determined from thermal forces due to Brownian motion; in active microrheology, the trapping laser's position is oscillated to apply forces. Accurate deduction of these forces by direct measurement of bead displacements requires that k is known. In prior optical trap methods, k is typically estimated before an experiment by calibration in a known viscous material, assumed to have the same refractive index n as the sample. This approach is inapplicable in vivo, since tissues are optically heterogeneous and the refractive indices are unknown a priori.

Starting from this framework, three measurements are obtained to calibrate the trap stiffness. To determine in situ calibration of each measured bead, three steps were performed: 1) detector sensitivity calibration, 2) detection of a trapped particle's (passive) thermal motion, and 3) detection of its (active) motion in response to force applied by oscillating the trap position. First, the change in volts per nanometer of bead displacement, $\beta$, is found for the detection QPD by piezo-stepping the bead through the detection laser beam. Second, the thermal power spectrum of the bead's motion $P_U(\omega)$ is recorded:

$$P_U(\omega)=\langle |\tilde{x}_U(\omega)|^2 \rangle, \qquad \text{equation (1)}$$

where $\tilde{x}_U$ is the Fourier transform of the undriven (passive) position data, and $\omega=2\pi f$, where f is the frequency. Third, the trap position is oscillated to drive bead displacement, and the active power spectrum $\tilde{R}_L(\omega)$ is recorded:

$$\tilde{R}_L(\omega) = \frac{\tilde{x}_{dr}(\omega)}{-i\omega \tilde{x}_L(\omega)}, \qquad \text{equation (2)}$$

where $\tilde{x}_{dr}(\omega)$ and $\tilde{x}_L(\omega)$ are Fourier transforms of the driven bead and trapping laser positions, respectively. Note that $\tilde{x}_{dr}(\omega)$ and $\tilde{x}_L(\omega)$ are complex, accounting for the relative phase of the trap and bead oscillations. Finally, the trap stiffness is found:

$$\kappa_\omega = \frac{\text{Re}\{\tilde{R}_L(\omega)\}}{P_U(\omega)}, \qquad \text{equation (3)}$$

where Re indicates the real component and $k_\omega$ is the trap stiffness at $\omega$. The trap stiffness should be constant over all frequencies. This allows measurement of both the trap stiffness in viscoelastic material and the local environment's complex shear modulus. As force is actively applied, this is an active microrheological technique. The friction relaxation spectrum can then be obtained with equation (4):

$$\tilde{\gamma}_D(\omega) + i\omega m = -\frac{\kappa_\omega}{i\omega}\left(\frac{1}{i\omega \tilde{R}_L(\omega)} + 1\right), \qquad \text{equation (4)}$$

and the complex modulus can be derived from the relaxation spectrum for spherical probes of a known radius R by equation (5):

$$G^*(\omega) = \frac{i\omega \tilde{\gamma}_D(\omega)}{6\pi R}, \qquad \text{equation (5)}$$

The complex modulus was measured at two sets of twenty multiplexed frequencies, one ranging from 3 to 101 and another from 300 to 15700 Hz. These sets of frequencies were primes (chosen to evenly cover the range of interest), or 100× a set of primes, to ensure distinct harmonics and prevent cross talk between frequencies. The amplitude of each component sine was equal. Thus, for the measurements, the trap is first actively oscillated, followed by a passive phase in which the trap is held stationary at the bead's equilibrium position. Although use of a complex waveform introduces noise, the multiplexing allows the frequencies to be recorded simultaneously, reducing measurement times. During the active pulse, the trap position is oscillated by a multiplexed waveform consisting of the sum of sines spanning a broad band of frequencies. After the trap is displaced according to the waveform, the probe motion is recorded with trap stationary during the passive pulse. To ensure that the amplitude of the resulting multiplexed waveform results in a maximum displacement of the probe that remains within the linear range of both the trap and detection beams, the component sines are given phase offsets. The frequencies were offset in phase by 0°, 45°, −45°, and −90°. The effect of the phase offsets is to reduce the stacking of the peaks of (especially the lower) frequencies so the probe is never moved more than 200 nm from its equilibrium position. Hence, all measurements were performed in the linear regime of the trapping and detection lasers. High frequency multiplexed data (>300 Hz) was acquired with 1 s (½ s active, ½ s passive) pulses for seven seconds, at an acquisition rate of 80 kHz. These data were then used to calibrate the trap, as the noise is minimal at higher frequencies in the passive spectrum, leading to more accuracy at the higher frequencies. Low frequency multiplexed data (<300 Hz) was acquired with 2-s pulses (1 s passive, 1 s active) for 20 s at an acquisition rate of 20 kHz.

Other Calibration Techniques Using the Power Spectrum to Obtain V-nm Calibration.

After trapping a bead in water, position data is acquired for 7 half-second pulses at 40 kHz. During this time the trap is oscillated at 500 Hz, with 50 nm amplitude. After this data is acquired, it is Fourier transformed into the frequency domain, and the power spectral density (PSD) of the data is taken for each pulse and then averaged over the pulses. This PSD is then fit with the equation:

$$P(f) = \frac{D}{\pi^2(f^2 + f_c^2)} + \frac{A^2}{2\left(1 + \frac{f_c^2}{f_{drive}^2}\right)}\delta(f - f_{drive}), \qquad \text{equation (6)}$$

where P(f) is the PSD, D is the diffusion coefficient, f is the frequency, $f_c$ is the critical frequency, and $f_{drive}$ is the frequency at which the trap is oscillating. After fitting, the volts-to-nanometers calibration for the detector and the trap stiffness can be determined from the fitted parameters. First, the volts-to-nanometers conversion is determined by the theoretical work ($W_{th}$, nm) in the oscillation peak divided by the experimentally measured work ($W_{ex}$,V) in the oscillation peak, $$\beta = \sqrt{\frac{W_{th}}{W_{ex}}}, \qquad \text{equation (7)}$$

where β is measured in nm/V, and $$W_{th} = \frac{A^2}{2\left(1 + \frac{f_c^2}{f_{drive}^2}\right)}, \qquad \text{equation (8)}$$

while $$W_{ex} = (P^{volts}(f_{drive}) - P_T^{volts}(f_{drive}))\Delta f, \qquad \text{equation (9)}$$

Here $P^{volts}(f_{drive})$ is the PSD in volts at $f_{drive}$, and $P_T^{volts}(f_{drive})$ is the thermal background at $f_{drive}$. Then the trap stiffness can be determined using the equation:

$$k_{ex} = 2\pi f_c \frac{\kappa_B T}{\beta^2 D^{volt}}, \qquad \text{equation (10)}$$

where $k_{ex}$ is the trap stiffness, $k_B$ is the Boltzman constant, T is the absolute temperature, and $D^{volt}$ is the diffusion coefficient measured in volts.

Bulk Rheology.

All bulk rheology measurements were carried out using an Anton Paar Physica MCR 301 rheometer equipped with a PP-25 measuring plate (parallel, 25 mm diameter). HA and Matrigel hydrogel samples were prepared by pipetting 450 ml of bead-ECM solution (stock Matrigel or pre-mixed HyStem chilled on ice) on Willco wells (GWSB-5040) containing a steel washer (1 mm thick, 25 mm inner diameter), and spreading the solution to fill the washer. The samples were then incubated at 37° C., in 5% CO2 for 90 min. 3 mL of PBS was added to the samples and they were incubated overnight. The next day, PBS was aspirated immediately before measurement. First, the top parallel plate was lowered to contact the surface of each sample until a load of 0.2 N was achieved. Frequency sweeps (0.1e10 Hz, 5 points per decade) were then conducted at three strains (0.1%, 1%, 10%). Finally, an amplitude sweep (0.1%-30%) at constant frequency (1 Hz) was performed to confirm that measurements were acquired in the linear range of viscoelastic deformation. Measurements were carried out in triplicate. The measurements are performed in an aqueous environment at room temperature.

Confocal Microscopy.

Images other than those captured on the trap were confocal images acquired using a Zeiss 780 LSM, using Zen software for data acquisition. Living zebrafish embryos were anesthetized using 0.4% buffered tricaine and then embedded in a lateral orientation in 1% low melting point agarose (NuSieve GTG agarose, Lonza). Live cell imaging was performed on zebrafish mounted in 4 or 8-well plates for time-lapse imaging to monitor development. Z stacks were acquired using a tiled approach and a 10× air objective of 0.3 NA where each individual image comprised 2046×2046 square pixels corresponding to 1416×1416 square microns for a total z distance of 276 microns. One Z stack was taken every 20 min from the time of injection to ensure regular development. Images of zebrafish probed on the trap were also taken, to determine the bead distribution in the entire fish.

Results

AMOTIV and Bulk Rheology Measure Similar Values for Amorphous Hydrogels.

Figure 4B:
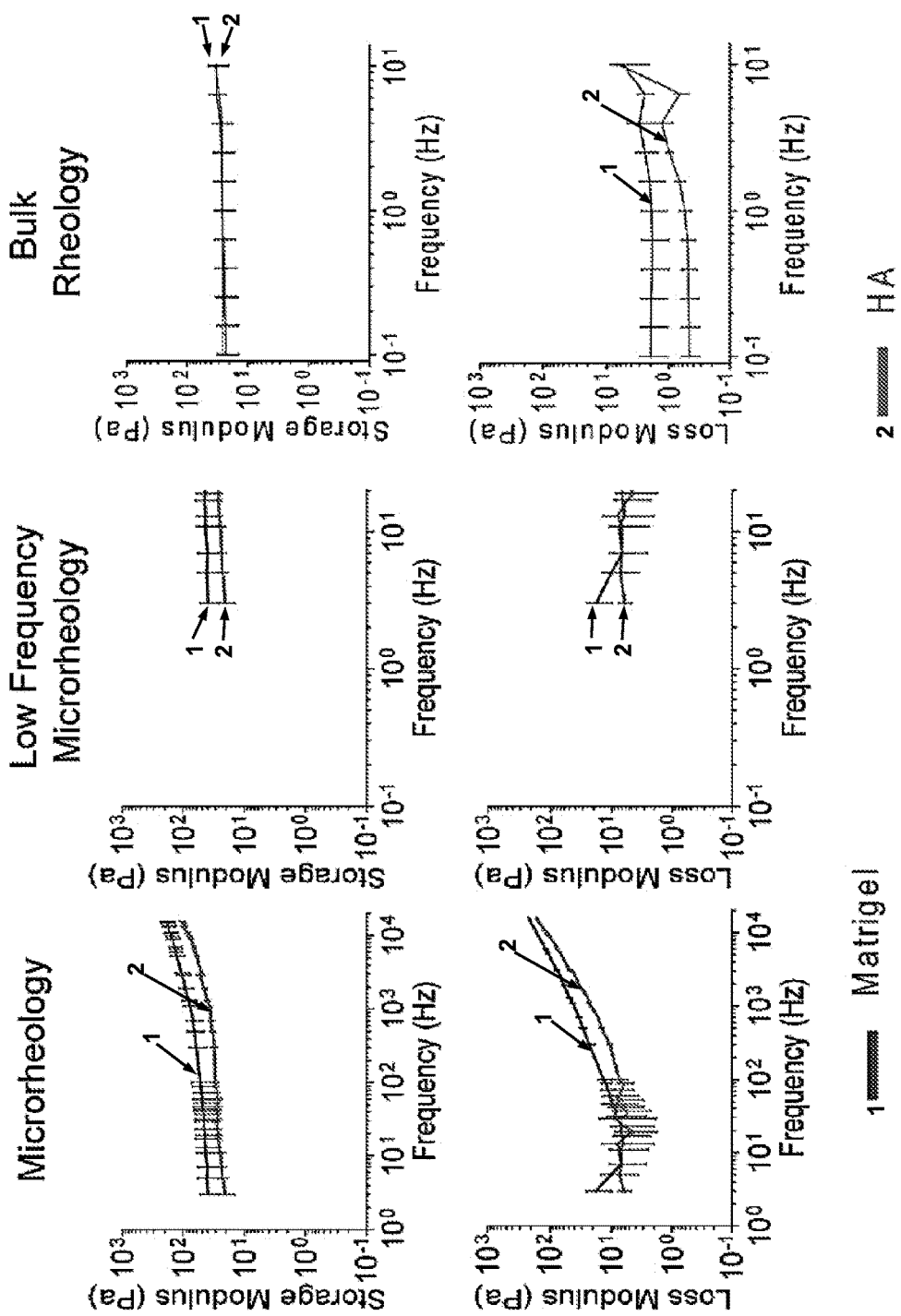
Figure 5A:
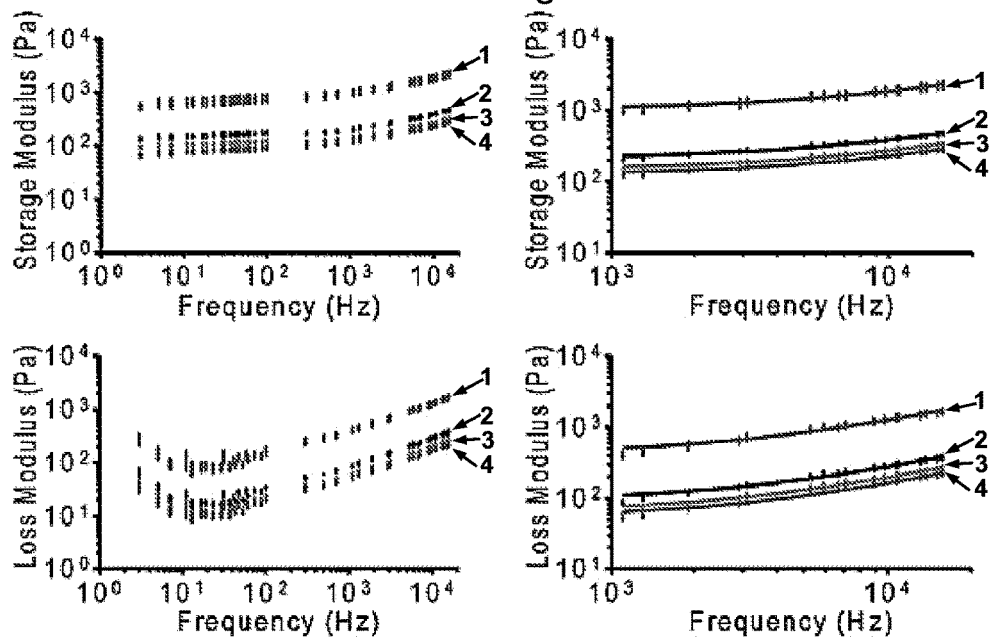
Figure 5B:
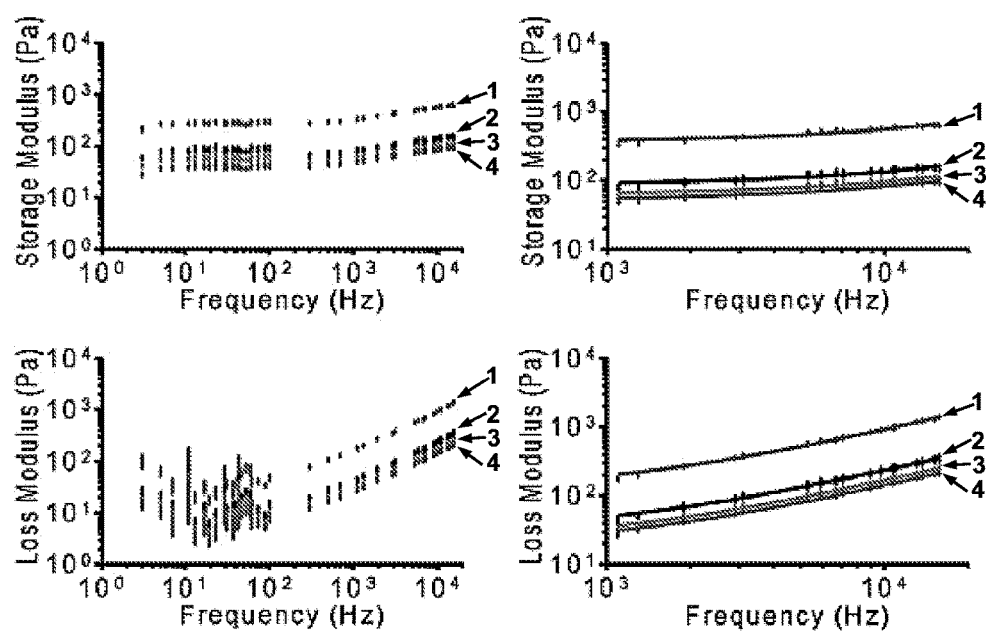
Figure 5C:
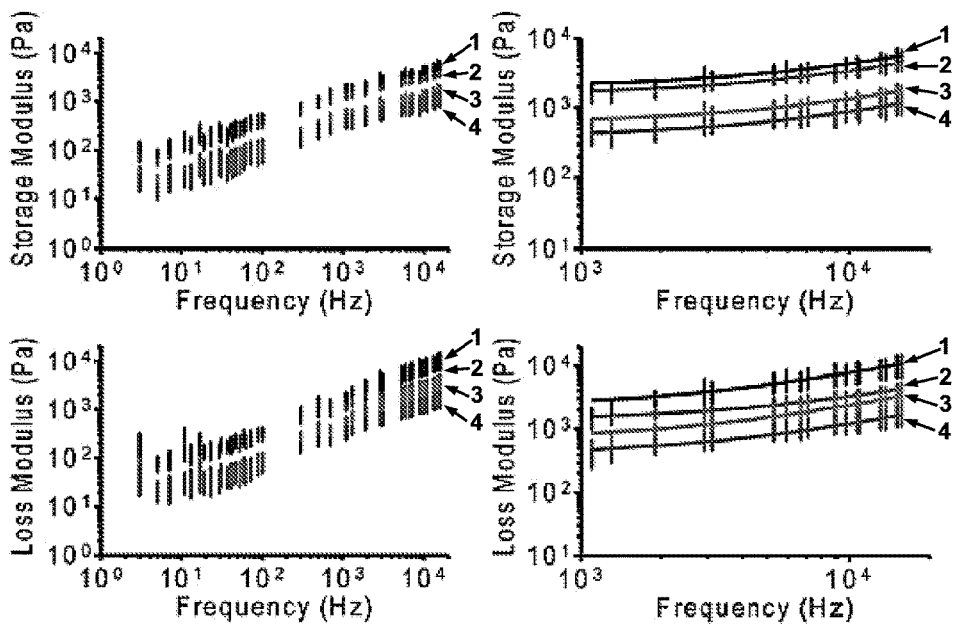
Figure 5C:
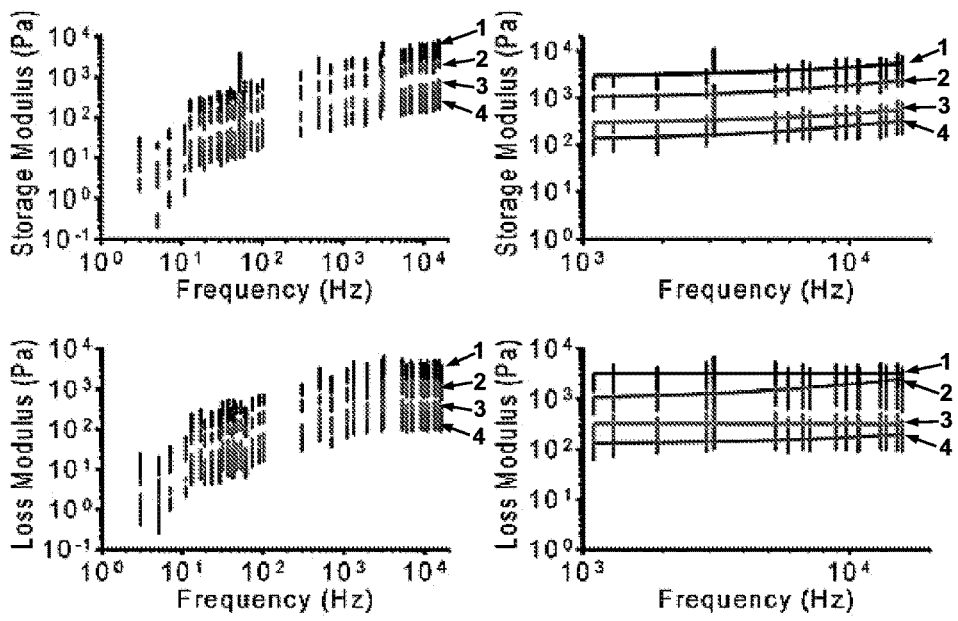

The relationship between microscale mechanical properties compared to bulk properties in materials of known extracellular matrix (ECM) composition and architecture was assayed using our optical set-up (see schematic shown in FIG. 4A). To avoid microscale heterogeneities, the complex shear moduli ($G^*(\omega)=G'(\omega)+iG''(\omega)$, with $G'(\omega)$ and $G''$ the storage and loss moduli, respectively) of uniform amorphous hydrogels, Matrigel and HA, was first measured (FIG. 4B). The measurements for the storage moduli agree quite closely with small angle oscillatory shear (SAOS) bulk rheology measurements in their common low frequency range, with elastic plateaus from ~10 to 100 Hz (Matrigel: $\overline{G'}_{10\text{-}100\ Hz}=47\pm4$ Pa, $\overline{G''}_{10\text{-}100\ Hz}=10\pm3$ Pa, HA: $\overline{G'}_{10\text{-}100\ Hz}=27\pm2$ Pa, $\overline{G''}_{10\text{-}100\ Hz}=7\pm2$ Pa) (FIG. 4B). Using the optical trap, it was possible to probe at higher frequencies than those attainable by bulk rheology. At higher frequencies, both hydrogels display weak power-law frequency dependence in $G' \propto \omega^\alpha$ and $G' \propto \omega^\beta$ (Matrigel: $\alpha$~0.31, $\beta$~0.59; HA: $\alpha$~0.34, $\beta$~0.72), increasing monotonically (Matrigel: $G'_{15kKz}$~185±82 Pa, $G''_{15kKz}$~214±11 Pa; HA: $G'_{15kKz}$~107±21 Pa, $G''_{15kKz}$~159±4.5 Pa) with $G''>G'$ at crossover frequencies of 9.5 kHz (Matrigel) and 5 kHz (HA).

Characterization of Tissue ECM In Vivo.

Next microscale zebrafish tissue mechanics were assayed. At the single cell stage embryo, carboxylated beads are injected and dispersed throughout the animal as the embryo develops. A widespread distribution of beads was observed. Some beads lie within the brain cavity as well as stuck along blood vessel walls throughout the brain, trunk and tail of the animal. Only beads that are fixed to the blood vessel wall were assayed, to probe the ECM lining of the vessels. Standard histological stains were also performed to show the distribution of common ECM proteins such as collagens, mucins and fibrins to show the complexity of the tissue microenvironment in the fish.

In Situ Calibration of Optical Trap Stiffness Accurately Resolved Tissue Heterogeneities In Vivo.

Figure 6:
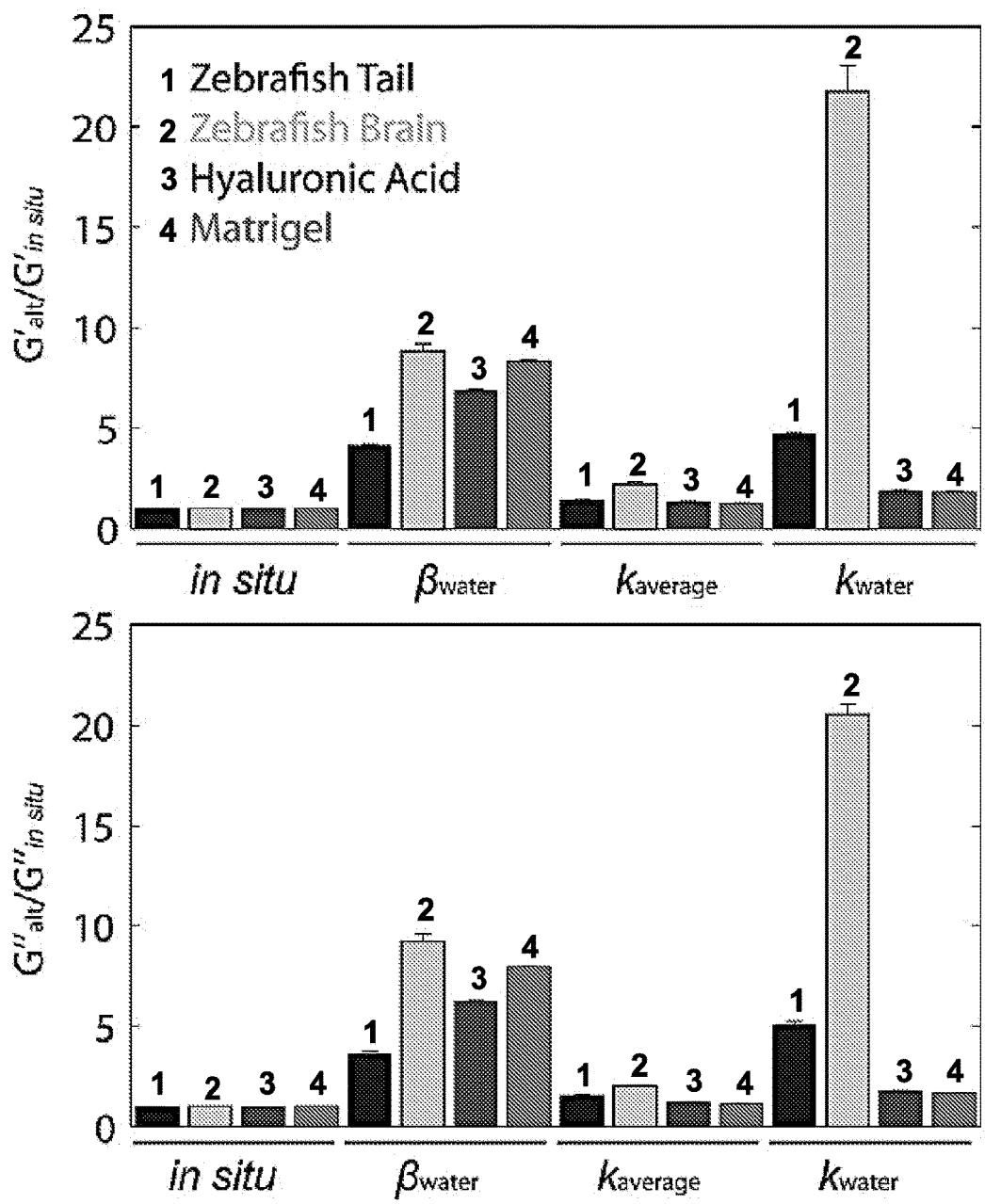
FIG. 6 is a set of graphs showing the estimation of complex moduli by calibration method. Calculation of G' and G" using the average trap stiffness (k) or average volts-to-nanometers conversion factor ($\beta$) from either the sample or from water results in overestimation of G' and G". At each measured frequency, the mean G' calculated from each calibration method was divided by the mean G' calculated from in situ calibration, yielding the overestimation factor; no frequency dependence was observed, so the values were averaged over all frequencies. Mean± standard deviation shown for each method applied to data from Matrigel, HA, zebrafish tail and brain. All alternate calibrations differ from our technique significantly ($p<10^{-26}$).

The optical setup was used to probe tissue mechanical properties in vivo by actively applying force to a bead, and then converting the bead's response relative to the driving force into the local viscoelasticity. One important step is the ability to calibrate trap stiffness accurately for each probe. In situ calibration was compared with other commonly used methods, some of which assume hydrogel and tissue samples have refractive indices similar to water, and that calibration of $\beta$ and $\kappa_\omega$ in water is sufficient for monodisperse beads in hydrogels and living zebrafish (FIG. 5). As can be seen in FIG. 5, previously used methods all lead to significant overestimation of the complex moduli, with high frequency linear fits showing significantly large differences in slope (p<0.01). This discrepancy could be due to the fact that beads in viscoelastic samples do not freely fall into the center of the trap as they do in water, which is important since $\beta$ and $\kappa_\omega$ vary along the beam axis. These issues were avoided by placing the trap on the bead center (found by centroid fitting the bead's Gaussian intensity profile). Additionally, the sample refractive index, n, may differ significantly from that of water. Hence, OT is calibrated in a viscous material with a similar n to that of the sample. This approach ignores any heterogeneity in bead size, trap properties due to differential scattering, and tissue refractive index. To perform this calibration, the $\kappa_\omega$ of each bead measured in situ ($\kappa_\omega$,bead) was averaged ($\overline{\kappa_\omega}$) and $\overline{\kappa_\omega}$ was used to calculate $G^*(\omega)$. In both thick hydrogels and distinct tissues of zebrafish larvae (brain and tail), the complex moduli calculated from $\kappa_\omega$ were significantly (p<0.01 when comparing the high frequency linear fits) greater (approximately two fold) than those calculated from $\kappa_\omega$,bead measured individually (FIGS. 5 and 6).

The discrepancy between methods was then determined by calculating the overestimation factor of G' or G" at each frequency relative to our method ($G_{calibration}(\omega)/G_{InSitu}(\omega)$), and then averaging over frequency to determine an average overestimation for each method. Using the corresponding $\kappa_\omega$ water, $\beta$ water, or $\kappa_\omega$ average to obtain the moduli leads to significant (p<0.0001 when comparing the normalized average values between calibrations) overestimation, up to 20-fold (FIGS. 5 and 6). Although averaging over each probe's trap stiffness in the sample gave superior results to the water calibrations, ignoring spatial heterogeneities still led to overestimation of the complex modulus.

Nonlinear Microrheology in 3D Hydrogels and Zebrafish.

Figure 7A:
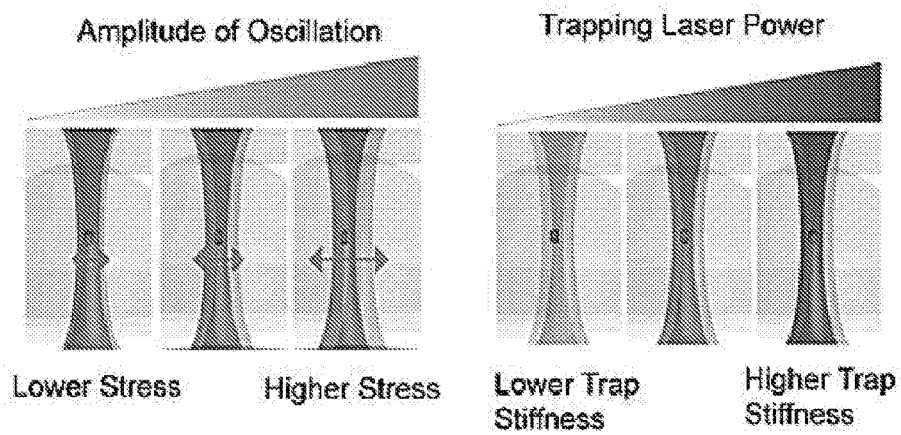
FIGS. 7A-7E show a schematic diagram and a set of graphs illustrating results from applying varied stresses using optical trap microrheology reveals differential responses in Matrigel and HA. (7A) There are two ways to vary the stress applied to the bead's microenvironment using the trapping laser: by changing the amplitude of the oscillation per frequency (left) and by changing the laser power (right). The maximum displacement of the bead can be likened to the strain induced in bulk rheometers. (7B-7C) show the response of Matrigel and HA, respectively, to these different types of stress (averaged over n>3 samples, # beads>15 per gel). One condition where only the amplitude of oscillation is changed (left, 2 nm and 20 nm) and the other where the trap laser power is changed (10 mW, 100 mW and 500 mW) at a constant amplitude of oscillation 20 nm (right) lead to significantly different values of G' (top) and G" (bottom) as determined by the non-parametric Friedman test $p<0.0001$. In addition, at about 1000 Hz, all data is fitted with a power law ($A\omega^B$), which revealed significantly different exponents at different powers for the storage moduli ($p<0.01$). Matrigel typically had exponents of approximately 0.3 in the storage modulus, and 0.6 in the loss moduli, HA storage moduli exponents ranged from 0.47 at 10 mW to 0.29 at 500 mW. The loss moduli were all around 0.7 however, near the expected value for a semi-flexible polymer. (7D-7E), Bulk rheology in HA and Matrigel at different strains for comparison to microrheology data (n=3 samples).
Figure 7B:
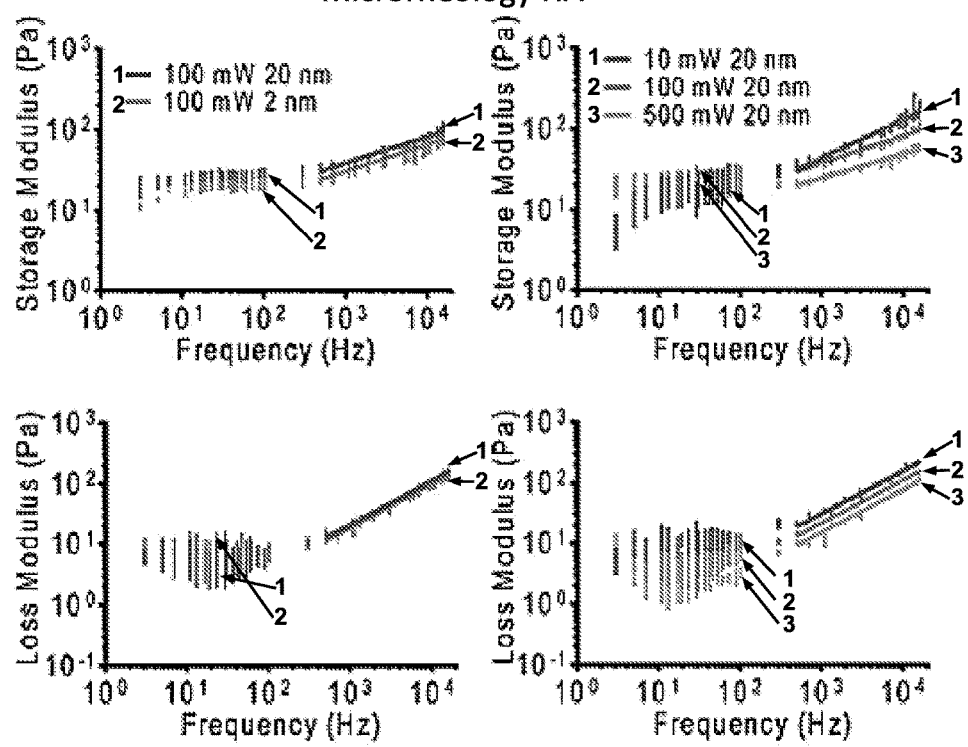
Figure 7C:
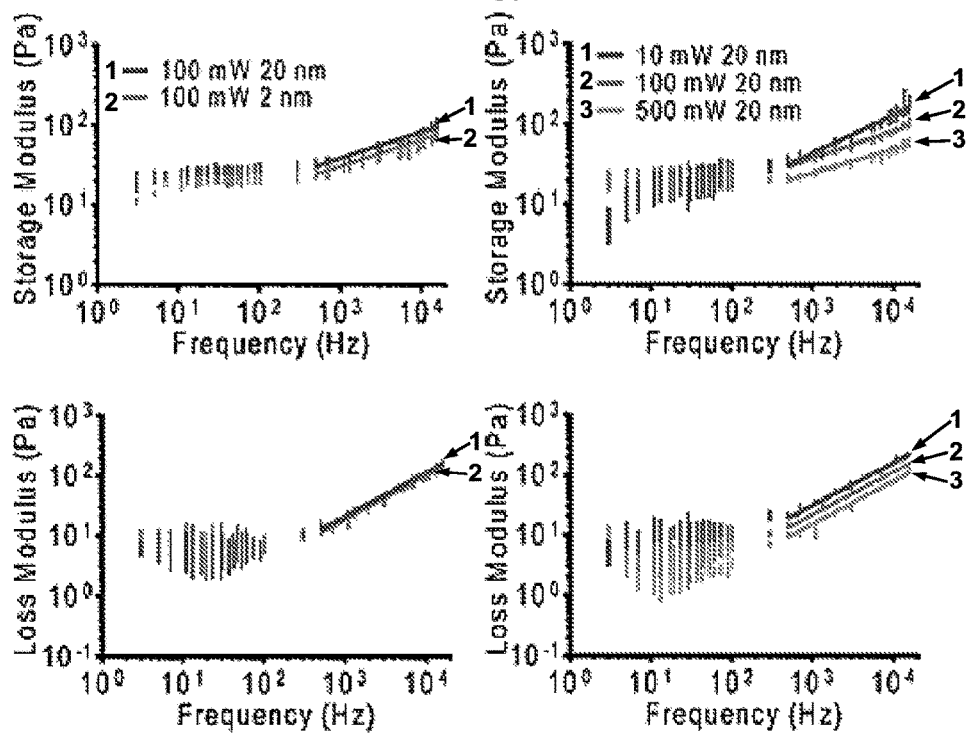
Figure 7D:
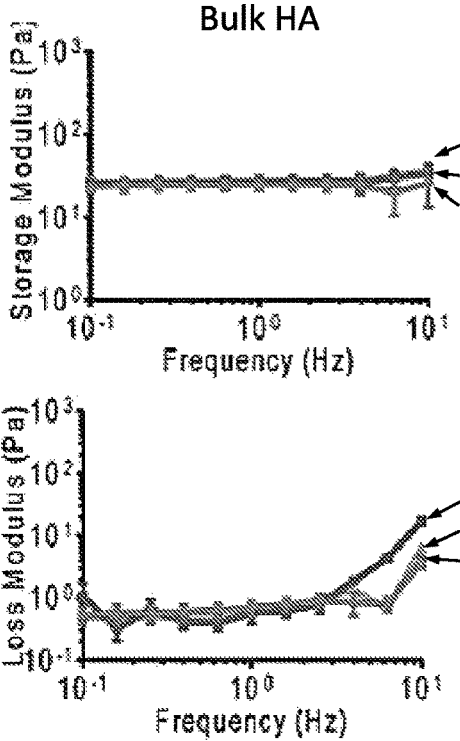
Figure 7E:
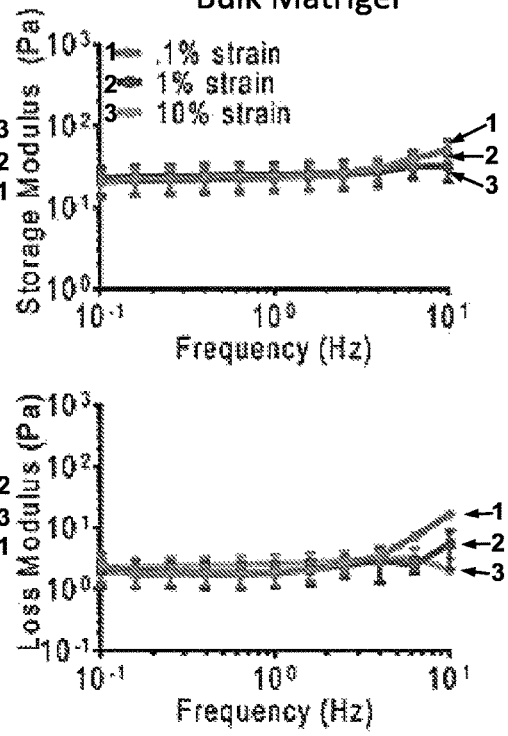
Figure 8A:
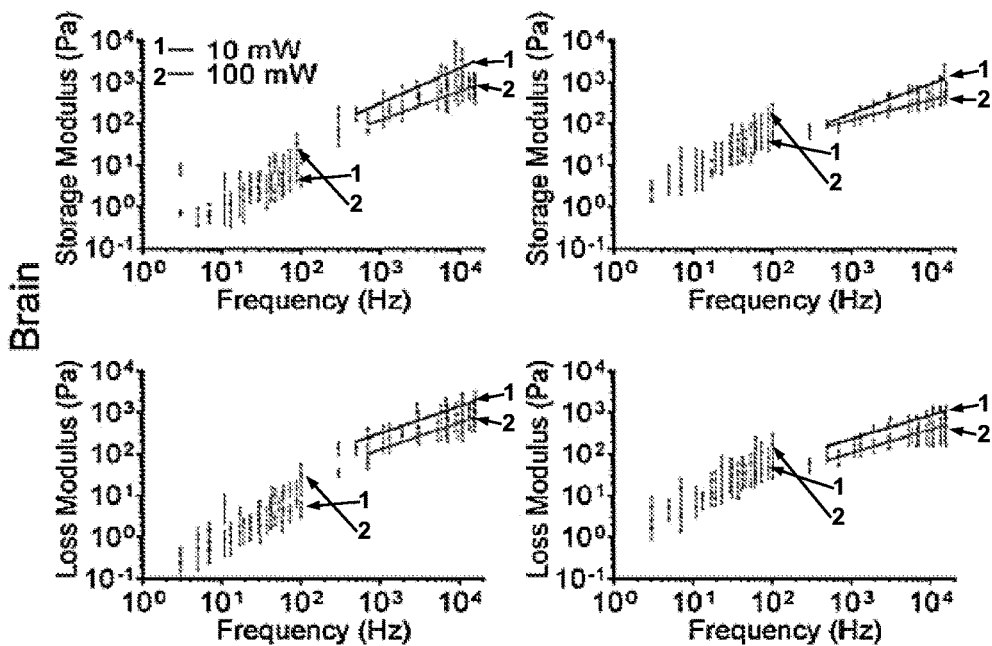
FIGS. 8A and 8B are a set of graphs showing that zebrafish tissue displays non-linear behavior with tissue viscoelasticity depending on the applied stress. Storage (elastic, top) and loss (viscous, bottom) moduli, measured for an average over n>3 zebrafish, number of beads>10 per tissue, per fish, located in the brain (8A) and tail (8B) at different trapping laser powers (10 mW (1); 100 mW (2); 500 mW (3)) where the amplitude of the bead oscillation is 2 nm on the left, and 2 nm on the right. Different oscillation and trap amplitudes in G' and G" in the tail or brain are significantly different as determined by the non-parametric Friedman test ($p<0.01$). The data also displayed a wide range of exponents from the power law fits, ranging from 0.4 to 0.8 in the various conditions. Graphs depict averages over samples (zebrafish or hydrogels), with the mean and (symbols)±standard error of the mean.
Figure 8B:
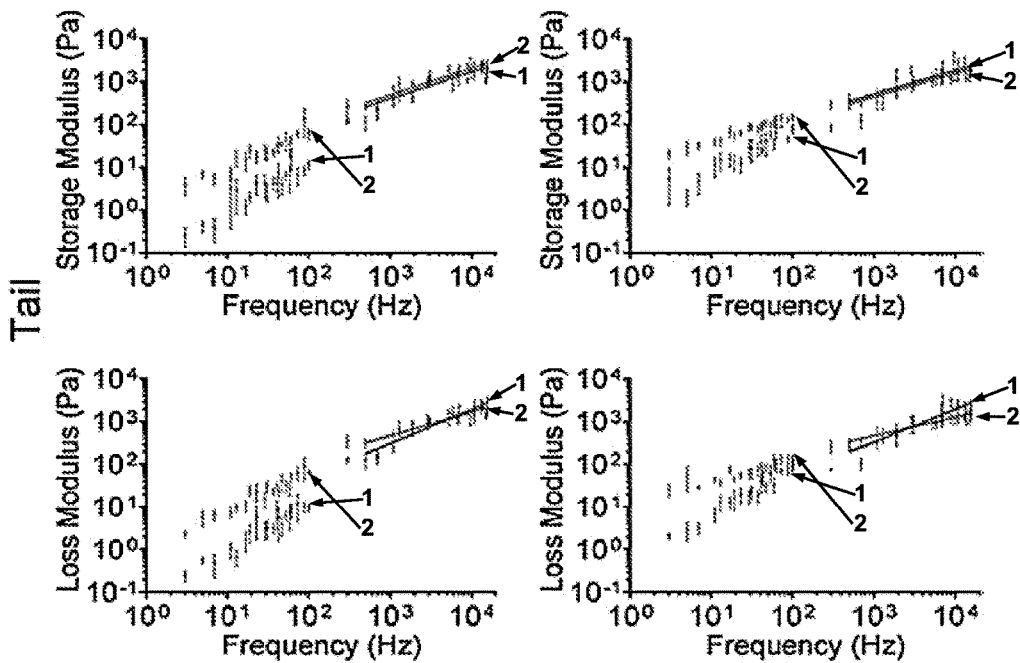

Biological materials often show stress-strain dependent viscoelastic response. Accordingly, the in vitro microscale stress-strain behavior was compared to the bulk properties to determine if non-linear behavior existed at the microscale that was not observed in the same material under macroscale examination. Stress-strain behavior in bulk rheology were obtained by varying the applied strain and performing frequency sweeps (0.1-10 Hz, 5 points per decade) at each strain (e.g. 0.1%, 1%, 10%). For an optical trap, there are two ways to vary the stress and strain applied to the probe's microenvironment: 1) by changing the trap position oscillation amplitude or 2) by changing the laser power (FIG. 7A). Since the applied force F and the displacement of the bead from the trap center Δx are related to the trap stiffness k by F=−kΔx, altering the oscillation amplitude or trap stiffness changes both the stress and strain applied to the gel. A greater frequency dependence of storage and loss moduli in Matrigel and HA acquired was observed at lower trap powers and lower oscillation amplitudes (FIG. 8). Interestingly, power law exponents fit to high frequency (>500 Hz) HA data cluster around 0.7 for the loss moduli, similar to what would be expected for semi-flexible polymer networks. However, in Matrigel, exponents cluster around 0.6, closer to the exponent expected for a flexible polymer network. Both Matrigel and HA elastic moduli display power law exponents <0.5, (Matrigel: 0.31-0.38; HA: 0.3-0.48). The power law exponent of the viscous moduli did not significantly depend on the trap power or oscillation amplitude in either material, but the elastic moduli in HA did significantly depend on trap power ($p<0.0001$), indicating nonlinear, stress-strain dependent behavior occurs in HA. In contrast, stress strain behavior measured by bulk rheology in HA and Matrigel mostly display constant elastic and viscous moduli at different strains, even though there are divergences even at low frequencies in the microrheology data (FIG. 7).

3D culture models are used to mimic the chemical and mechanical properties and dimension of in vivo tissue architecture. However, in vivo tissues may show variations in mechanical properties, not only due to spatial heterogeneities, but non-linear behaviors that amorphous 3D ECM models fail to display. Additional assayed were performed to determine if tissues display behaviors similar to those observed in 3D hydrogels similar to known polymer theories. Comparison of microscale stress-strain behavior at varying trap powers and amplitudes in the zebrafish display regime-dependent polymer dynamics (FIG. 8) where power law exponents fitted at high frequencies (>500 Hz) ranged 0.5-0.8. Interestingly, at trap power of 10 mW, the tail and brain of the zebrafish have loss moduli power law exponents of 0.76 and 0.66 (~semi-flexible), while at 100 mW, they are 0.44 and 0.5 (approaching flexible behavior). Similarly, the elastic moduli of the tail and brain at 10 mW have loss moduli power law exponents of 0.63 and 0.73, respectively, compared to 0.5 and 0.48 at 100 mW (FIG. 8). In zebrafish, over half of the power law exponent fits show significant trap power dependence ($p<0.01$), as opposed to hydrogels, where only the HA's elastic moduli showed such a dependence. This indicates significantly that more non-linear behavior exists in living tissue than is present in 3D culture models.

Discussion

To test the validity of the in situ calibration disclosed herein, it was reasoned that amorphous, uniform hydrogels would enable the most direct comparison between bulk rheology and microrheology. Comparable values were observed for the storage loss moduli using both the microscale and bulk techniques. However, there was approximately an order of magnitude difference between the micro and bulk measurements (FIG. 4). A non-limiting explanation for this finding is that it may be due to microdomains that affect the local viscosity that may not be resolvable in the bulk measurements.

Knowing the trap stiffness (and thus the applied force) for each probe enables interrogation of the mechanical response to force as a function of stress and strain amplitude within thick hydrogels and in vivo. In situ calibration at each probe was shown to improve accuracy, and temporal and spatial resolution sufficiently to resolve in vivo tissue heterogeneities. Previous studies to characterize in vivo tissue dynamics in animal models such as zebrafish (*Danio rerio*), fruit flies (*Drosophila Melanogaster*), and nematodes (*Caenorhabditis elegans*) have largely relied on measurements based on passive microrheology due to thermal fluctuations. Specifically, the passive cytoplasmic characteristics of zebrafish and other embryos have been discussed, but the precise and absolute rheological properties of the tissue microenvironment have not been previously attained. Here the first in vivo characterization of zebrafish tissue rheology is provided.

The multiplexed waveform to modulate the trapping laser's position was comprised of a sum of sines at multiple frequencies, which reduces time for data acquisition. Prime numbers can be used for the input sine waves as the higher order harmonics of prime frequencies do not overlap, thus reducing crosstalk between frequencies during active oscillations. In particular, the waveform of the trap position was a linear combination of the twenty frequencies with equal amplitudes. The measurement was broken into two separate waveforms of 20 multiplexed frequencies because of the concern of leaving the linear regime of the viscoelastic response, as well as the linear response of the QPD. As a consequence, the maximum total displacement from the equilibrium position of the bead did not exceed 200 nm. As such, all measurements at all frequencies were conducted in the linear regime. Strictly speaking, the bead is simultaneously experiencing oscillations at each multiplexed frequency, and therefore as its displacement varies throughout the course of the waveform, it is the case that the trap displacement is equal for each frequency. The bead displacement at each frequency is variable, and is part of the measurement. It would not be possible to a priori know the bead displacement given a specific trap displacement prior to the measurement, as the bead's response to the trap is what is being measured. The subtlety here is that with this type of multiplexing, the perturbation occurring at each frequency can be viewed as having a fixed amplitude but with a varying amount of prestress, which is a function of the composite waveform. However, the average prestress is zero. The phase offsets of 0, 45, −45, and −90 degrees are used to reduce the maximum displacement of the trap so that the bead never leaves the linear regime of the trapping or detection laser beams. This is increasingly evident at lower frequencies, where if the same phase is used for all frequencies the peaks would "stack" to a greater degree in the multiplexed waveform. When there were no phase offsets, then there will be cross talk at higher harmonics.

In light of the fact that application of prestress can indeed alter the mechanical response in comparison to a non-prestressed situation, before undertaking this approach we performed comparisons between the shear moduli resulting from multiplexed measurements and standard single-frequency measurements in the same samples. Exemplary data is provided in FIGS. 10 and 11. While the results are not indistinguishable, it is believed that that in the context of the aggregate measurement error, the increase in statistical power gained by increased sample size due to reduction in measurement times attributable to multiplexing outweighed the discrepancy due to the introduction of this prestress.

Using the disclosed optical trap system and method it was possible to probe a greater dynamic range (frequencies spanning from 1 Hz to 15 kHz) than those probed using most bulk rheological instruments. This range covers time scales that are relevant for understanding the effect of the microenvironment on faster processes such as protein-protein interactions, cytoskeletal remodeling, molecular motor activity (which in turn affects slower processes such as 3D cell motility), cell proliferation and the establishment of multicellular structures.

The disclosed optical trap apparatus and method was compared with other methods, which assume hydrogel and tissue samples have refractive indices similar to water or lack heterogeneity, and that calibration of β and $\kappa_\omega$ in water is sufficient or that an average calibration could be applied to the entire sample. These other methods led to significant overestimation of the complex moduli (FIGS. 5 and 6).

Microscale stress strain behavior in uniform amorphous hydrogel also showed differences as a function of applied stress that were not observed at overlapping frequencies of bulk rheological measurements. These data reinforce the need to examine different spatial, temporal and force regimes to fully assess the effects on tissue behavior. Also, it was demonstrated that in vivo tissue mechanical properties are distinct from those seen in ECM hydrogels as determined by microscale stress strain behavior. In particular, living tissue's mechanical response is more stress dependent than 3D hydrogels, as at low stress it displayed behavior similar to semiflexible polymers, while at higher stresses behaved similar to flexible polymers. The differences measured at different trap powers and oscillation amplitudes indicate that we may be probing a different regime of mechanical behavior than the bulk measurement, likely due to the fact that our microrheological measurements subject a small region of the sample to stress much greater than that applied by bulk rheometers which distribute the stress over the entire sample.

Figure 10A:
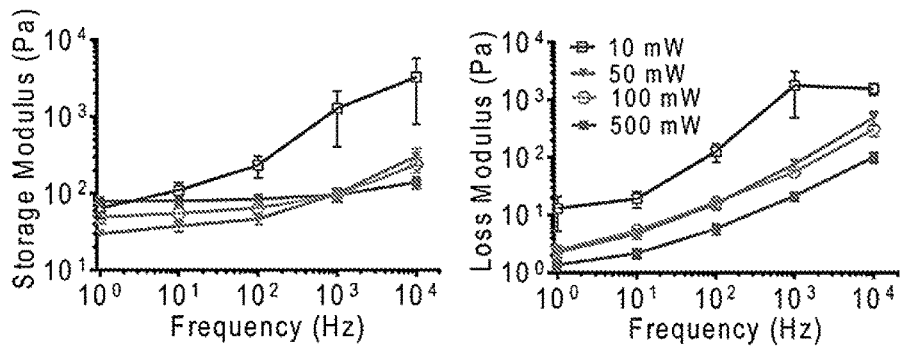
FIGS. 10A and 10B are a set of graphs showing a comparison of single frequency sweeps to multiplexing of frequencies in Matrigel at different laser powers. Modulation of trapping power allows the probing of different material properties and gives the equivalent of stress strain curves required to quantitate force responses in materials. In addition, multiplexing gives comparable measurements to single frequency sweeps.
Figure 10B:
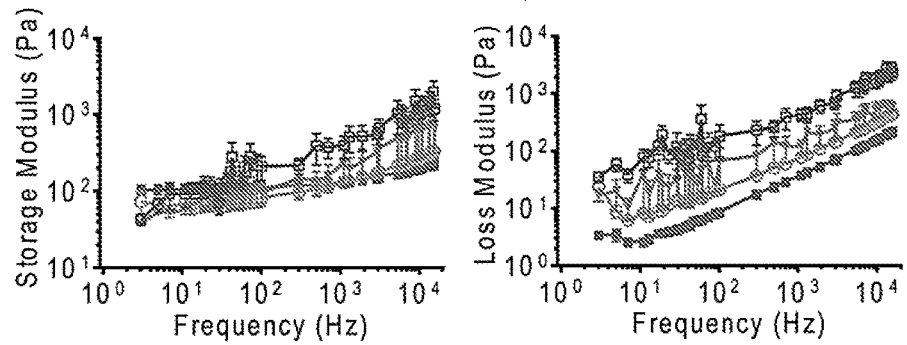
Figure 11A:
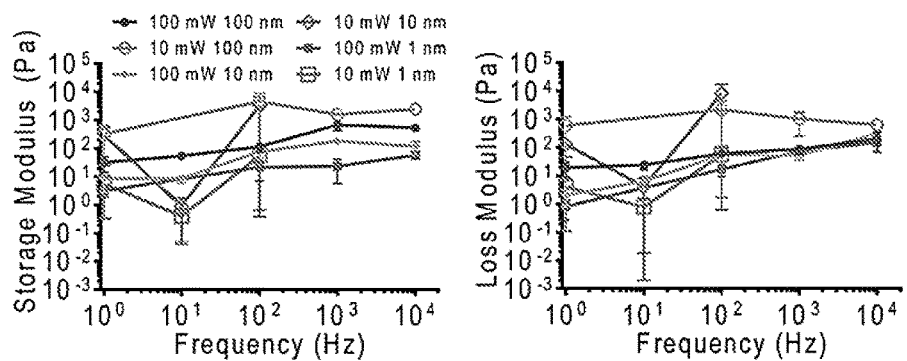
FIGS. 11A and 11B are a set of graphs showing a comparison of single frequency sweeps to multiplexing of frequencies in Matrigel at different laser powers in the zebrafish. Modulation of trapping power allows the probing of different tissue properties and gives the equivalent of stress strain curves required to quantitate force responses in materials. In addition, multiplexing gives comparable measurements to single frequency sweeps.
Figure 11B:
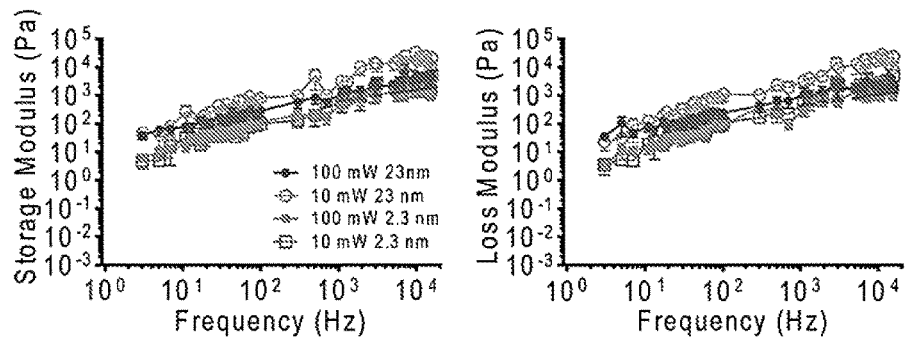
Figure 12A:
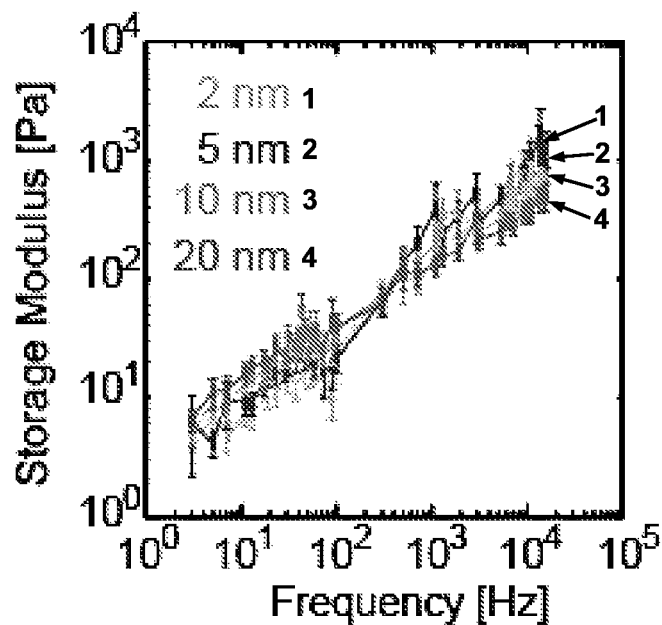
FIGS. 12A-12D are a set of graphs illustrating that in situ-calibrated optical trap based active microrheology resolves nonlinear stress-strain behavior in tumor samples. Active microrheology of excised murine subcutaneous melanoma tumors. B16-F10 metastatic mouse melanoma cells or MDA-MB-231 breast cancer cells were subcutaneously injected with fluorescent polystyrene microspheres into the flank and tumors were allowed to grow for 2 weeks. Animals were sacrificed and tumors were excised, rinsed, and thin sections (~70 µm) prepared on glass bottom dishes for measurements. (12A and 12B) Storage (12A) and loss (12B) moduli vs. frequency at oscillation amplitudes 2 nm (1), 5 nm (2), 10 nm (3), and 20 nm (4) for B16-F10 metastatic mouse melanoma cell tumor samples are shown. Additionally, the Complex modulus vs. frequency (G' and G") for (12C) B16-F10 metastatic mouse melanoma samples or (12D) MDA-MB-231 breast cancer cell tumor samples using Oscillation amplitude of 20 nm per frequency is also shown.
Figure 12B:
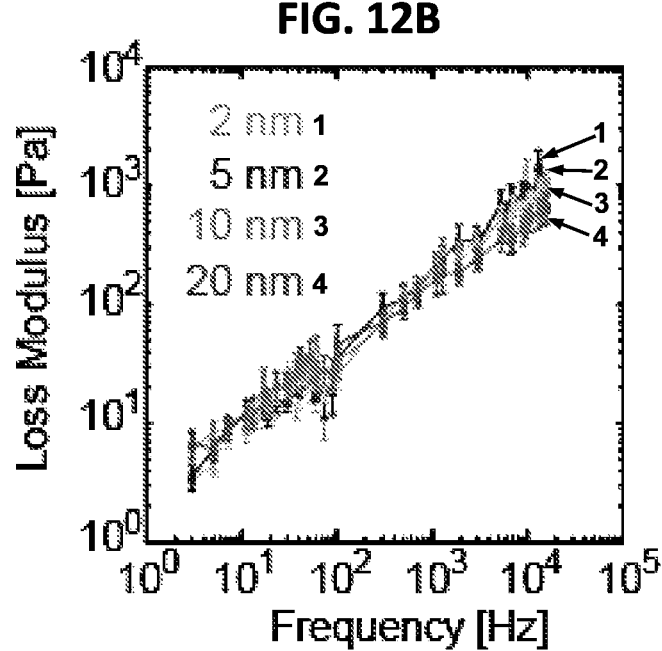
Figure 12C:
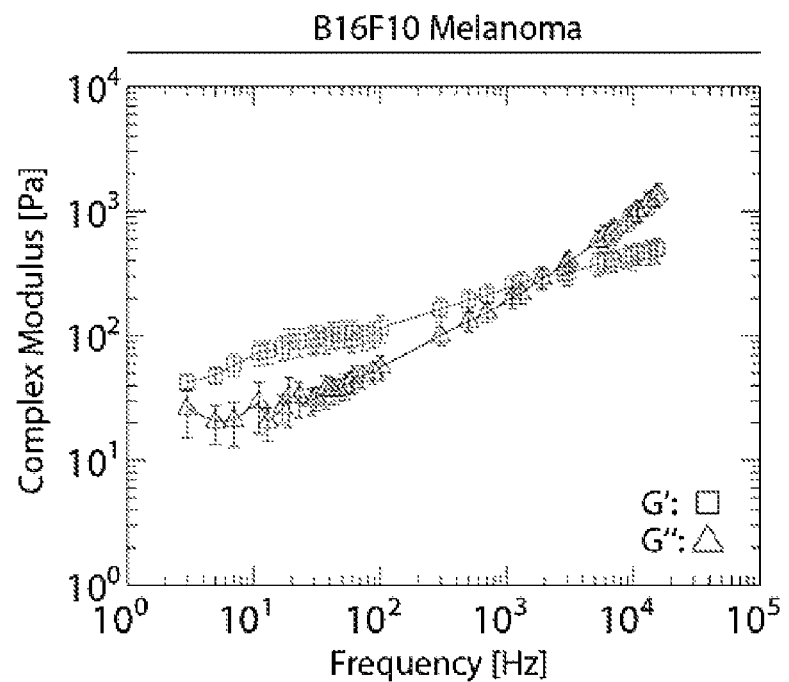
Figure 12D:
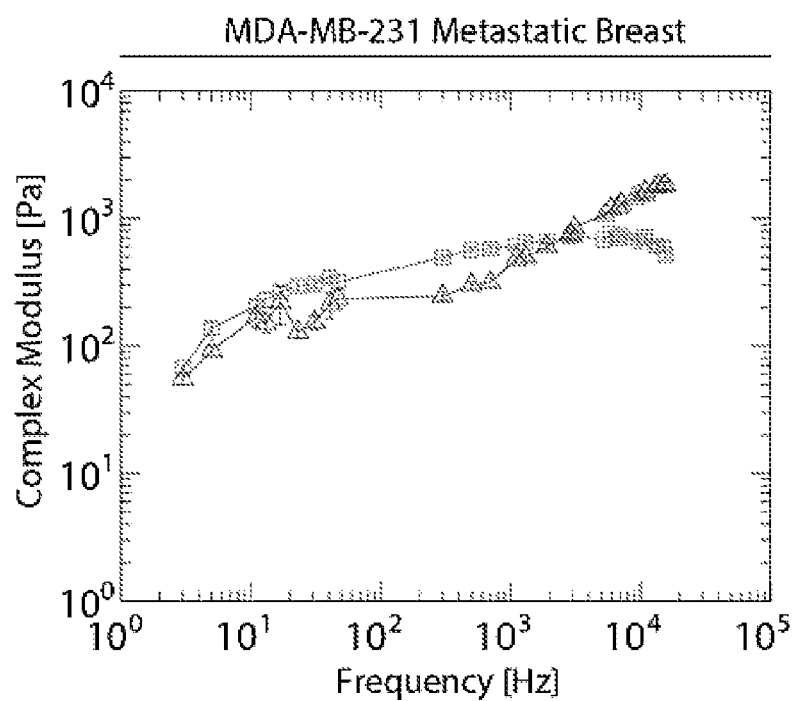

One consideration when varying laser power is the effect of localized heating as the power is increased. In The disclosed optical trap system and method, the 1064 nm CW laser induced heating, which results in ~8 K/W heating at the focus, based on previous studies. Thus, laser power of 100 mW corresponds to ~0.8 K. At higher powers this begins to matter more, especially in the effect on the power spectrum, which is obtained by applying a Lorentzian fit to determine the trap stiffness. Additionally, heating may also reduce the fluid viscosity, but this will depend on the material and the effects on protein matrix or tissue are even less established for obvious reasons. These effects can be seen as laser powers are increased to 500 mW as shown in FIG. 10.

The optical tap beads used in this example were 1 µm carboxylated microspheres, and did not freely diffuse in any of the samples on the assayed experimental time-scales, indicating that they are larger than the local microenvironment's mesh size. Therefore the disclosed methods assay the protein polymer mesh that makes up the local ECM microenvironment of the cell, and not only the surrounding fluid phase.

Example 2

In Situ Calibrated Mechanical Properties of Ex Vivo Tumor Microenvironment

This example illustrates use of the optical trap method and system disclosed in Example 1 to obtain microrheological data from tumor samples ex vivo. It was found that mouse melanoma tumors and human breast tumors displayed complex moduli ~5-1000 Pa, increasing with frequency and displaying a nonlinear stress-strain response. Direct calibration of trap stiffness at each probe allows the determination of absolute forces needed to resolve local heterogeneities in tumor samples. Thus, the disclosed microrheology methods can be used to provide a mechanical biopsy as a diagnostic tool to aid in design of therapeutics that would be complementary to those based on standard histopathology.

Materials and Methods

Microsphere PEGylation.

Fluorescent 1 µm carboxylated polystyrene spheres conjugated to Rhodamine (Thermofisher #8821) were centrifuged and resuspended in 10% molar excess EDC (1-ethyl-3-(3-dimethylaminopropyl)-carbodiimide) for 1 h. The beads were centrifuged and resuspended in 50× molar excess ethylene diamine for 6 h and agitated on a shaker at medium speed overnight. Beads were then centrifuged and resuspended in a solution containing 2× molar excess mPEG-SVA adjusted to pH 8 with NaOH overnight, then agitated on a shaker overnight. Beads were centrifuged and resuspended in deionized water.

Ex Vivo Tumors

Cell Lines.

Tumor cell lines, a mouse melanoma cell line, B16F10 (cat. No. CRL-6475) and a human breast adenocarcinoma cell line, MDA-MB-231 (cat. No. HTB-26) were obtained from American Type Culture Collection (ATCC, VA). Briefly, both cell lines were cultured as monolayers in DMEM high glucose media (Life technologies, CA) supplemented with final volume of 10% Fetal Bovine Serum (FBS), 1% MEM non-essential amino acids, L-glutamine, penicillin and streptomycin. Medium was refreshed every 2-3 days.

Lentiviral Transduction.

Cells were transduced with virus using the ExpressMag Transduction System (Sigma). Briefly, viral supernatant was incubated with magnetic beads at room temperature for 15 min, added to the adherent cells and placed on a strong magnetic plate at 37° C. for 12 min. Media was replenished 16 hr. later and the viral mixture disposed of in compliance with NIH policy. Transduced cells were selected with 2 µg/ml puromyocin (InvivoGen, San Diego, Calif.). Flow cytometry was performed to isolate the GFP/luciferase positive cells from cells that did not the express these markers using the Cell Sorting feature on a BDFACS Aria (BD Biosciences).

In Vitro Bioluminescence Activity Assay.

Luciferase activity of pre-sorted cells was determined using VivoGlo™ luciferin (Promega, Madison, Wis.), according to the manufacturer's instructions. Briefly, $1 \times 10^4$ of GFP/Luciferase and its parental cells were seeded on a white-walled 96-well plate (Corning, Corning, N.Y.). Cells were washed with PBS and then mixed with 150 µl/ml of luciferin in IMDM media (Gibco). After 10 minutes, luciferase activity was measured by Infinit200® Pro Luminometer (Tecan, San Jose, Calif.). For each experiment, 3 individual samples were prepared.

Tumor Injections.

Briefly, a cell and fluorescent bead suspension in PBS was injected subcutaneously in the flanks of 8-10 week old female nu/nu mice where the final cell number was $5 \times 10^5$ cells and $10^7$ beads. Tumor burden was estimated by weekly physical and in vivo bioluminescence measurements and mice were euthanized as tumors approached 1 cm in diameter with no detectable metastasis, as determined from BLI imaging. Luminescence emitted by tumors in nude mice was measured weekly. Briefly, each mouse was injected intraperitoneally with 100 µl of VivoGlo™ luciferin at 3 mg/ml in PBS. Mice were imaged on the dorsal and ventral sides and the luciferase signals were captured by a Xenogen IVIS-200 system (Perkin-Elmer, Waltham, Mass.). The luminescence quantity was displayed by radiance and the units are displayed as photons/s/cm²/sr.

Ex Vivo Tumor Preparation.

Fresh tumors were excised and half of the sample was prepared for ex vivo imaging and the other for histological analysis. Half of the tumor was immediately placed in 4% paraformaldehyde solution for 12 h and then prepared for histological staining Tumors were then embedded in paraffin prior to sectioning on a microtome. Serial sections, 8 µm thick were labeled for specific ECM stains as delineated by Masson trichrome, and Haematoxylin and eosin as previously described (Blehm et al., 2015). The second half was then thinly sliced and mounted on a No. 0 Willco glass bottom dish to perform mechanical measurements.

Optical Trap-based Microrheology was performed as described in Example 1.

Results

The complex moduli of the tumors was measured using the disclosed optical trap based active microrheology. To confirm similar stages of tumor progression for each sample, the absence of distant metastasis was confirmed using bioluminescent imaging (BLI) and visual examination of organs at necropsy. B16-F10 melanoma tumors exhibited a nonlinear mechanical response; storage moduli differed significantly ($p<0.004$) with oscillation amplitude (2 nm, 5 nm, 10 nm, 20 nm). Complex moduli ($G^*$) exhibited weak power law frequency dependence with power law exponents of 0.70, 0.63, 0.57, and 0.52 at amplitudes 2 nm, 5 nm, 10 nm, and 20 nm, respectively. Storage and loss moduli rise monotonically 5 Pa-1000 Pa over frequencies 3 Hz-15 kHz, (FIG. 12). MDA-MB-231 breast tumor samples had similar mechanical properties (FIG. 12).

Discussion

The active microrheology measurements described here of the murine tumor microenvironment are the first of their kind. Fluorescent beads and fluorescence microscopy were used to avoid inadvertent measurement of vesicles and other small round objects in the tumor. Such objects can be trapped and measured, but careful consideration of their surface moieties and size is needed to determine accurate displacement-viscoelasticity conversions.

Atomic force microscopy (AFM) has been used to assess the elastic modulus of individual collagen fibers and collagen rich tumor stroma ex vivo. AFM micro- and nano-indentation gives a higher spatial resolution compared to bulk rheological methods, allowing examination of individual fibers and/or superficial mechanical mapping of tissues. Elegant studies have shown that an increase in Young's modulus is indicative of the malignant transformation during human breast tumor progression with the largest value at the invasive front. Plodinec and co-workers conducted AFM indentation measurements with sharp tips on human breast tumors measured at frequencies ~0.8-1 Hz, finding a trimodal distribution of Young's moduli with peaks at ~1, 2, and 6 kPa (Plodinec, Loparic, Monnier, Obermann, Zanetti-Dallenbach, Oertle, Hyotyla, Aebi, Bentires-Alj, H., et al., 2012). AFM indentation measurements on human breast tumors measured at 20 µm/s with a 5 µm spherical probe showed Young's moduli ~1 kPa (Acerbi et al., 2015). Interestingly mouse melanoma cell and human breast cancer cell tumors measured herein were as much as two orders of magnitude softer at comparable frequencies. It was determined that mouse melanoma tumors also exhibited nonlinear stress-strain behavior, with frequency dependence shifting from semi-flexible to flexible behavior with increasing stress-strain amplitude, as obtained for collagen hydrogels. In addition, it was determined that mouse melanoma tumors and human breast tumors displayed elastic moduli ~5 to ~1000 Pa, increasing monotonically with frequency. Mouse melanoma tumor samples also exhibited nonlinear stress-strain behavior in the tumor, with frequency dependence shifting from semi-flexible to flexible behavior with increasing stress-strain amplitude.

Example 3

In Situ Calibration of Position Detection in an Optical Trap for Active Microrheology in Viscous Materials In optical trapping, accurate determination of forces requires calibration of the position sensitivity relating displacements to the detector readout via the V-nm conversion factor ($\beta$). Inaccuracies in measured trap stiffness (k) and dependent calculations of forces and material properties occur if $\beta$ is assumed to be constant in optically heterogeneous materials such as tissue, necessitating calibration at each probe. For solid-like samples in which probes are securely positioned, this can be achieved by moving the sample with a nanopositioning stage and stepping the probe through the detection beam. However, in many samples a different method is needed. Here, we introduce a simple method to find $\beta$ in any material by steering the detection laser beam while the probe is trapped. We demonstrate the approach in the yolk of living *Danio rerio* (zebrafish) embryos and measure the viscoelastic properties over an order of magnitude of stress-strain amplitude.

As disclosed herein optical trapping can be applied in three-dimensional (3D) tissue microenvironments in vivo to interrogate viscoelastic response over a broad range of frequencies, and can be used to probe stress-strain behavior by modulating the forces on the trapped particle (active microrheology), which is of interest since many biomaterials and specimens exhibit nonlinear viscoelasticity. Accurate determination of these forces requires knowledge of the optical trap stiffness, k, and the probe's displacement from equilibrium, $\Delta x$. Determining $\Delta x$ can be accomplished by calibrating the position sensitivity, $1/\beta$, of the detector, which relates the detector readout (in volt) to the probe's displacement (in nanometer). Measuring forces in biological materials including tissues is non-trivial because both k and $\beta$ vary from probe to probe throughout the sample due to intrinsic optical and mechanical heterogeneities.

FIG. 13A depicts an microrheology measurement scheme employing active-passive calibration described in Examples 1 and 2, in which mechanical properties of viscoelastic samples are determined from the thermal power spectrum and the active power spectrum (obtained by oscillating the trap position). An advantage of this approach is that the optical trap stiffness, k, is determined in situ from the spectra of each probe. However, $\beta$ is not given by the spectra and requires an additional measurement for samples like the optically heterogeneous tissues of the zebrafish embryo (FIG. 13B). This example provides additional methodology for determining $\beta$ in viscous materials.

A common and effective way to measure probe displacements in optical traps is by back focal plane interferometry (See, e.g., Denk and Webb, *Appl. Opt.*, 29(16) 2382-2391 (1990); and Allersma et al., *Biophys. J.*, 74(2) 1074-1085 (1998), each of which is incorporated by reference herein). When a probe of diameter d is trapped at the center of the beam waist of a laser with wavelength $\lambda$ focused by an objective in its image plane, some light undergoes scattering due to light-probe interactions and (in the dipole limit $d<\lambda$) produces spherical waves. This scattered light slightly diverges from the fraction of light that does not undergo scattering. Thus, shifts in relative phase between these two wavefronts give rise to a pattern of constructive and destructive interference. A high numerical aperture (NA) condenser collects this light, and is placed in Köhler illumination such that the image planes of the field diaphragm iris and the objective are conjugate and image into each other (forming a Keplerian telescope). Behind the condenser, a dichroic mirror reflects the detection beam (but not the trap beam or lamp light) onto a detection lens that is positioned to relay the image at the back focal plane of the condenser onto a QPD. In this configuration, displacements of the probe cause rotation of the detection beam in the image plane and corresponding translations of the beam at both the back-aperture of the condenser and on the detection QPD. The interference pattern is mapped onto the QPD; so lateral displacements of the probe relative to the detection beam in the imaged plane result in changes in voltage. The voltage response $\Delta S$ is linearly related to probe translations for small displacements ($\Delta x \pm \sim 150$ nm from the probe center). Thus, calibrating the position detection sensitivity consists in finding the V-nm relation $\Delta x = \beta \cdot \Delta S_x$ in the linear response regime.

A number of methods may be used to calibrate $\beta$, each applicable in various situations (FIG. 13C). When the temperature and the Brownian dynamics of the probe and material are known, methods based on recording the thermal power spectrum are frequently used, but are generally inapplicable to microrheology since they depend on independent knowledge of the dynamic viscosity or related frictional terms (FIG. 13C (1)). Additionally, biomaterials may exhibit glassy dynamics and are out of thermal equilibrium. In another method, the trap is moved rapidly while the impulse response of the QPD is tracked as the probe relaxes to its new position, but this too relies on the drag coefficient. In materials where a priori knowledge of the physical properties of the tissue is not known, determination of $\beta$ requires other methods. Tolié-Nørrelykke et al. demonstrated that by imposing a known oscillating flow in combination with the power spectrum method, both the drag coefficient and $\beta$ can be determined (Tolié-Nørrelykke, et al., *Rev. Sci. Instrum.*, 77(10), 2006). This approach requires that the induced motion in the liquid be synchronized with an imposed low frequency stage oscillation (an AOD oscillation would also work), which may not be the case in biphasic materials, and will not work in samples that show nonlinearities or elastic effects. A direct method is to scan the probe across the waste of the detection beam by employing a piezoelectric nano-positioning system (NPS) to step the sample stage with known displacements (Allersma et al., *Biophys. J.*, 74(2) 1074-1085, 1998). This 'piezo method' requires calibration of the NPS, which can be accomplished by imaging displaced probes with a camera of known pixel size (FIG. 13C (2)). This method works in nonlinear or elastic materials where the probe motions are confined and remain correlated to the stage displacements, including some tissues with fine meshwork. However this is not the case in more fluid-like environments, wherein yet other methods must be used.

This example provides beam steering approach, but uses a weak secondary detection beam to scan across the probe while it is confined in the trap (FIG. 13C (3)). This method is therefore applicable to probes that are either weakly attached to or freely moving through the microenvironment, such as in the perivascular microenvironment in the zebrafish trunk depicted in FIG. 13B. It also works for probes that are strongly attached or confined in a solid-like microenvironment, and the microenvironment may be non-linear, viscous, elastic or viscoelastic with unknown Brownian dynamics. The method produces independent measurements of $\beta$ in good agreement with the power spectrum method and the piezo scanning method.

Optical Trap

Figure 14:
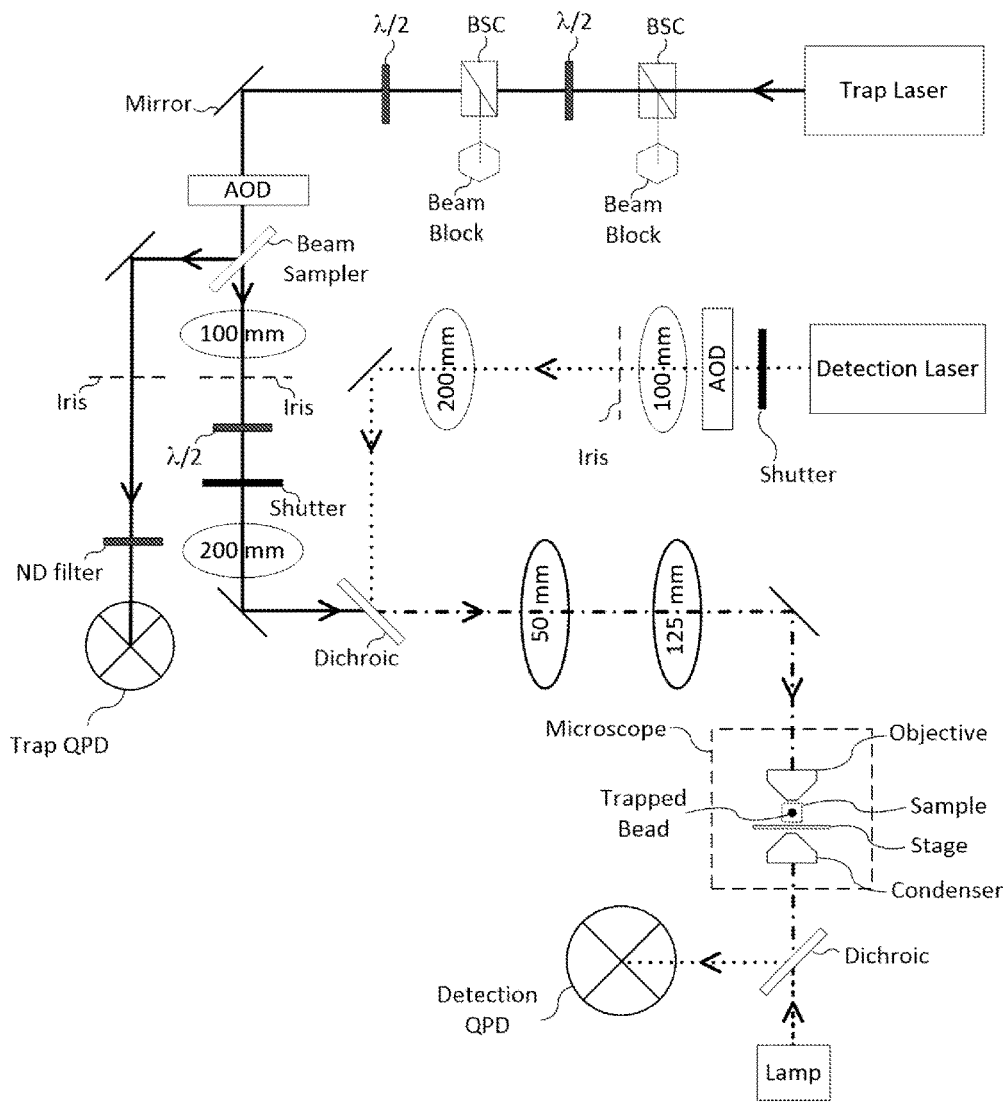
FIG. 14 is a schematic diagram of an exemplary optical trap system. Both the trap beam and the detection beam have two dimensional acousto-optical deflectors (AOD) in the optical path, along with the two telescope lens pairs (one pair is shared for both beams after the dichroic) for collimation and mapping images onto the detection QPD. With this system, a probe can be trapped and the detection beam is steered across it while the detection QPD signal is recorded to calibrate β. Then trap beam can be alternately oscillated and held stationary in a sequential measurement for both the active-passive calibration of trap stiffness and for broadband active microrheology measurements.

The optical trap setup is depicted in FIG. 14. A trapping beam and a detection beam are each steered with dual axis AODs, where the (1-1) diffracted (1st order in both dimensions) beam is selected with an iris. Prior to experiments, the Hz-nm relations of the AODs are calibrated by attenuating and focusing the beam on a coverslip and imaging the backscattered beam on a CCD camera. To detect trap displacement, the beam is split with a beam sampler mirror directly after the acousto-optic deflector (AOD) to direct a small amount of power onto the 'trap' QPD. This QPD is not in a conjugate plane, so changes in QPD voltage are correlated to beam displacements. A high numerical aperture (NA), long working distance (WD) condenser that collects all light from the objective. Behind the condenser, a dichroic mirror decouples the trap beam and lamp light from the detection beam which is sent through a relay lens that is positioned to image the back focal plane of the condenser onto the detection QPD. Time-correlated trap and probe QPD signals are recorded on a FPGA (field programmable gate array) DAQ (data acquisition) card, which also controls TCXO (temperature controlled crystal oscillator)-generated radio frequency (RF) signals that drive the AODs. Control and data collection are conducted in custom LabVIEW programs.

Before each experiment, beams are aligned and tested using a control sample of carboxylated beads in water. First the trapping beam is oscillated and centered on the trap QPD by adjusting the relay mirror between the trap QPD and the beam sampler mirror. Next a bead is trapped, the trap is oscillated, and the detection beam is co-aligned with the trapping beam by adjusting the dichroic mirror that couples the trapping and detection beams. Oscillation and adjustment is conducted iteratively in each lateral dimension. Finally, the detection QPD is adjusted so the signal from a trapped bead in equilibrium falls on its center. After beam alignment the thermal power spectrum is recorded (blocking with eight separate measurements) while the trap is oscillated at 500 Hz with amplitude of 50 nm. The viscosity and $\beta$ are calculated from the spectrum by fitting to a Lorentzian to ensure that the measured viscosity of water is accurate and that the positional sensitivity is consistent with previous values specific to the setup and alignment of the microscope. Finally, the bead position on a charge-coupled device (CCD) camera is determined by centroid-fitting an image of the bead on the camera, and this position is used as the lateral trap position.

With the beams aligned, measurements are then conducted in the sample material. A probe is selected and brought to the lateral trap position by moving the piezo stage. With the objective focus in the specimen plane, the condenser is adjusted to Köhler illumination. The probe is then axially centered in the trap by stepping the objective vertically through 49 steps, recording a bright field image with the CCD camera at each step, and moving the probe to the plane with the highest intensity image. The stage, trap, and probe are held stationary, and the detection beam position is oscillated sinusoidally at a frequency $f_{drive}$ of 1 kHz with a displacement amplitude of 54.7 nm for a measurement time $t_{msr}$ of 1 s across the center of the probe while the detection QPD voltages are recorded at a sampling rate of 80 kHz. The resulting voltage time series are then Fourier transformed into the frequency domain with a frequency bandwidth $\Delta f$ of 1 Hz, giving a voltage frequency spectrum, which exhibits a strong peak at $f_{drive}$. Because the drive period (1 ms) divides evenly into $t_{msr}$, the peak is a single datum rather than having finite width. The voltage at $f_{drive}$ is then divided into the displacement amplitude of the detection beam to give β in nm·V$^{-1}$. The process can be conducted consecutively in each dimension.

Following β calibration, a set of measurements are conducted to give both k and the complex modulus and complex viscosity of the microenvironment as a function of the stress-strain amplitude (A, in nm displacement) and frequency (ω) at which the trap is oscillated, G*(Δ, ω) and η*(Δ, ω), respectively. The measurements consist of separate recordings of the power spectra of the probe during passive motion (during which the trap is stationary) and active motion (during which the trap is oscillated over a range of frequencies) to get the active and passive power spectra substantially as described in Example 1. In active measurements, the trap was displaced by a waveform consisting of the superposition of 20 sine waves of equal amplitude at frequencies ranging 2 Hz-12,863 Hz (a set of logarithmically distributed prime numbers to ensure distinct harmonics. The frequencies were alternately offset in phase by 0°, 45°, −45°, and −90° to minimize the maximum trap displacement, which was 200 nm, within the linear regime of the trapping and detection lasers. Each probe was subject to 7 sequential pulses, where each pulse consisted of 2 s active motion followed by 2 s passive motion. In all samples, only probes at distances exceeding ~30 μm away from the cover slip surface were measured to minimize drag in consideration of Faxén's law.

Animal Studies.

Wildtype and transgenic (Tg(fli-1:eGFP)/Tg(gata-/:dsRed)) zebrafish (*Danio rerio*) were maintained at 28.5° C. on a 14 h light/10 h dark cycle according to standard procedures. Embryos were obtained from natural spawning and raised at 28.5° C. and maintained in egg water containing 0.6 g sea salt per liter of DI water. 2 nL of monodisperse of 1 μm rhodamine carboxylated fluospheres (Thermofisher #F8821) at 5×10$^8$ beads/mL in sterile PBS was microinjected into the zebrafish embryo yolk. Between 10 and 16 h post fertilization (hpf), embryos were transferred to egg water supplemented with phenylthiourea (PTU, Sigma P5272), suspended at 7.5% w/v in DMSO, at 1 part in 4500 to inhibit melanin formation and increase optical transparency. Embryos were then returned to the incubator at 28.5° C. and checked for normal development and widely dispersed beads daily using fluorescence microscopy. Mechanical characterization was performed 48 h post fertilization (hpf). Zebrafish embryos were anesthetized using 0.4% buffered tricaine, then embedded in a lateral orientation in 1% low melting point agarose (NuSieve GTG agarose, Lonza), and allowed to polymerize on a 50 mm glass-bottom dish with cover glass no. 1.5 thickness. Egg water supplemented with tricaine was added to the agarose hydrogel for the entire time of data acquisition and used as the immersion medium. The maximum time of data acquisition on each embryo did not exceed 4 h.

Silicone Solutions.

Polydimethyl siloxane (PDMS) (Dow Corning Sylgard 184 silicone elastomer base) was combined with Sylgard 184 silicone curing agent at a 10:1 ratio in a weighing boat on a digital scale. 20 μl of bead/sterile PBS solution of 5×10$^8$ beads/mL of monodisperse 1 μm rhodamine carboxylated fluospheres (Thermofisher #F8821) was added during 10 min of thorough mixing with a pipette tip. A flow chamber was made using two strips of double sided scotch tape, a No. 1.5 cover slip and a microscope slide. With vacuum pressure applied to one end of the chamber a small volume of the solution was pulled in from the other end so no air bubbles remained. Samples were measured immediately and only within 30 min of initial mixing. Basement membrane ECM hydrogels (Matrigel (Corning (#354230, Lot #3032578))) were prepared as described in Example 1. Rat tail collagen I hydrogels (BD Biosciences, San Jose, Calif., USA) were prepared as previously described (see, Artym and K. Matsumoto, *Curr Protoc Cell Biol.*, 10-18 (2010); Staunton et al., *Sci. Rep.*, 6, 19686, 2016).

Results

Figures 16A, 16B:
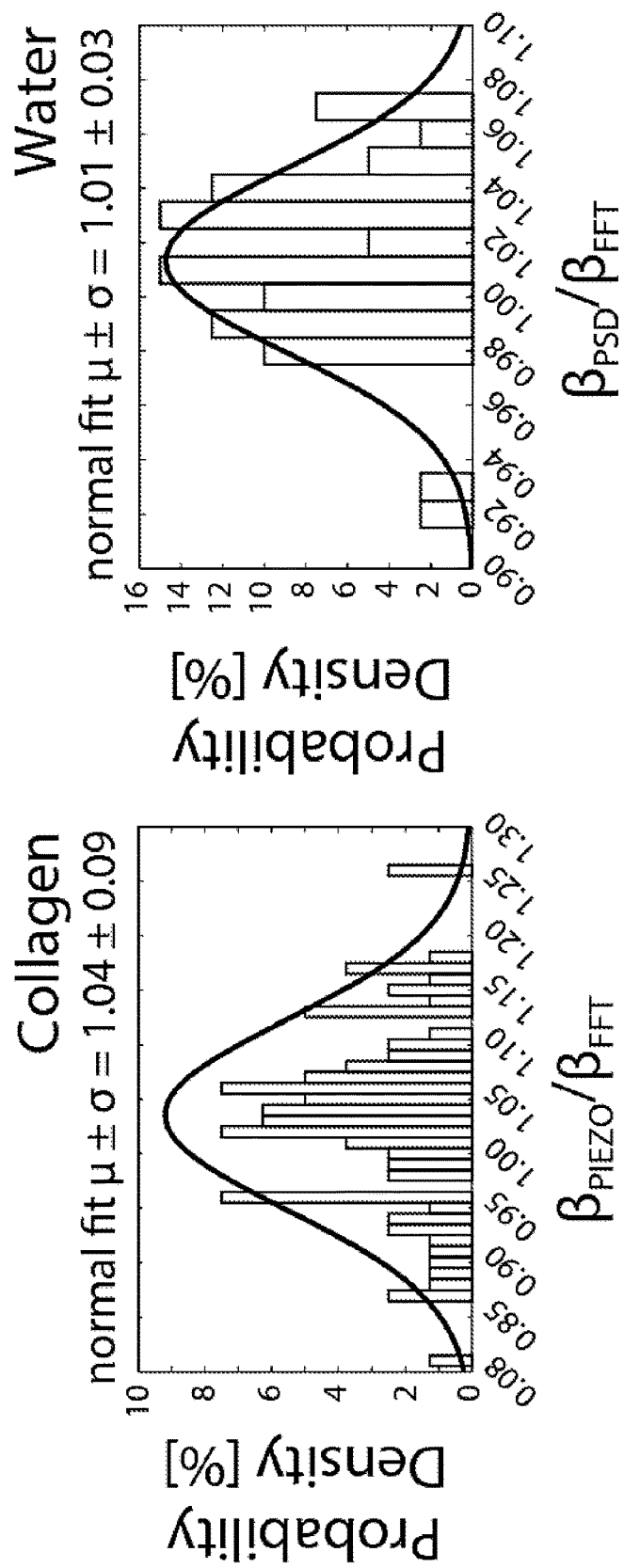
FIGS. 16A-16B are a set of histograms showing results from V-nm conversion factors (β) of carboxylated polystyrene microspheres in water and hydrogels obtained by PSD and FIT methods. Each probe was trapped and passive motion was recorded, Fourier transformed and fitted to a Lorentzian power spectrum model with the drag coefficient of water to calculate β. Then the detection beam was oscillated across the probe center with frequency 1 kHz and amplitude 54.7 nm, Fourier transformed and used to calculate β. (16A) comparison of values from both methods. (16B) Misapplication of the PSD method in elastic or viscoelastic materials results in overestimation of β values by as much as factors of nearly 100. $\beta_{PSD}/\beta_{FFT}$ is tightly centered near unity with the PSD method only 1% greater on average, with standard deviation and coefficient of variation <4%.

FIG. 15 shows example data comparing β calibrations by the piezo stage stepping and detection beam steering methods of a probe injected into a zebrafish embryo located in a solid-like region of the tail (FIG. 15A, FIG. 15C) and another probe in a fluid-like region of the yolk (FIG. 15B, FIG. 15D). During piezo calibration, the probe in the tail was confined and moved in tandem with the piezo stage (FIG. 15A). The resulting QPD signal, in V, in the dimension parallel to the stage movement is plotted against the position in nm. β is determined simply by fitting a line in the central, linear response region (±~150 nm from the probe center). Multiple samples of the voltage are averaged before fitting to reduce noise. This is performed in each lateral dimension. The piezo calibration fails for unconfined probes. The resulting signal for the probe in the yolk was very noisy, which possibly moved completely out of the detection beam path (FIG. 15B). To overcome this limitation, the detection beam steering (FFT) method was employed. The method works both for confined probes (FIG. 15C, zebrafish tail) or unconfined probes (FIG. 15D, zebrafish yolk). Noise present at low frequencies is avoided by oscillating at a single high frequency. Signal-to-noise ratio can be improved by increasing the collection time, or by averaging a number of separate measurements. In cases where the piezo method is applicable, FFT and piezo results agree well. For confined 1 μm diameter carboxylated polystyrene microspheres embedded in rat-tail type I collagen hydrogels (2 mg·ml$^{-1}$ initial concentration; polymerized at 37° C.), both methods were used to calculate (FIG. 16A). The ratio of the two values was taken for each probe, with a value of 1.04±0.09 (Gaussian fit parameters, mean±standard deviation), a discrepancy falling below the range of other sources of error. In cases where the thermal power spectrum (PSD) method is applicable, the FFT method produces results in agreement with the PSD method. The values of β determined by the FFT and PSD methods were compared for probes in water and in surrogate basement membrane extracellular matrix hydrogels, assuming the drag coefficient of water in both cases. As expected, the PSD method cannot be used in elastic or viscoelastic materials such as reconstituted surrogate basement membrane extracellular matrix hydrogels, as the drag coefficient is incorrect and the spectrum does not fit a Lorentzian function. When calculated under these inappropriate conditions, values for β were found to be as much as nearly 100-fold greater than those calculated for the same probes by the FFT method. However, in water (FIG. 16B), the two methods produce remarkably similar values. The PSD method resulted in values 1% greater on average than the FFT method, with a standard deviation under 4%.

Figure 17C:
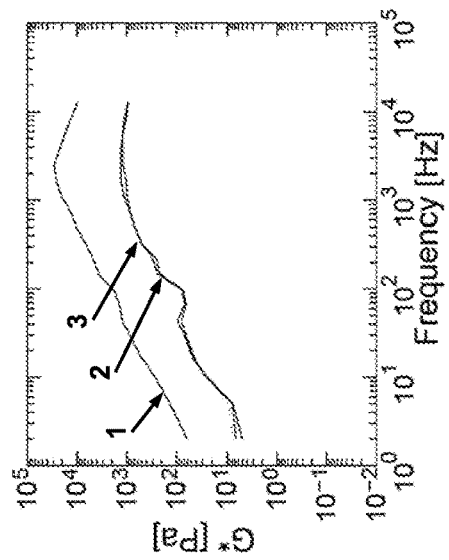
FIGS. 17A-17F. Active Microrheology data of probes in uncured PDMS (17A-17C) and injected into the yolk of a zebrafish embryo at 48 h post fertilization (17D-17F). Measurements were conducted from 2 Hz-12,863 Hz, with multiplexed frequencies at stress-strain amplitudes of 2 nm, 5 nm, and 20 nm (trap displacements) per frequency to probe the stress-strain behavior (17A,17D) Elastic component of the complex shear modulus. (17B,17E) Viscous component of the complex shear modulus. (17C,17F) Magnitude of the complex shear modulus. The moduli increased significantly with increasing stress-strain amplitude (p<0.0001, two-way ANOVA).
Figure 17B:
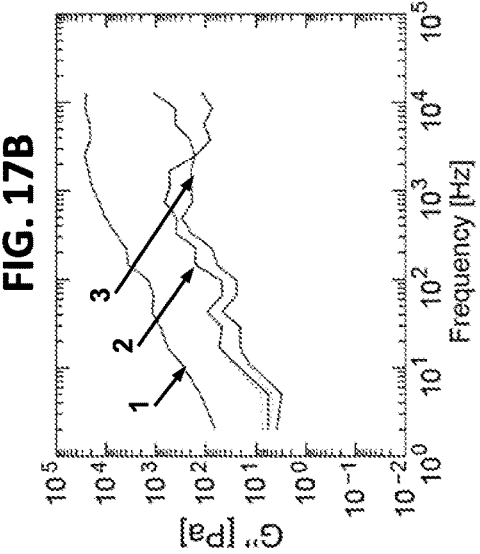
Figure 17A:
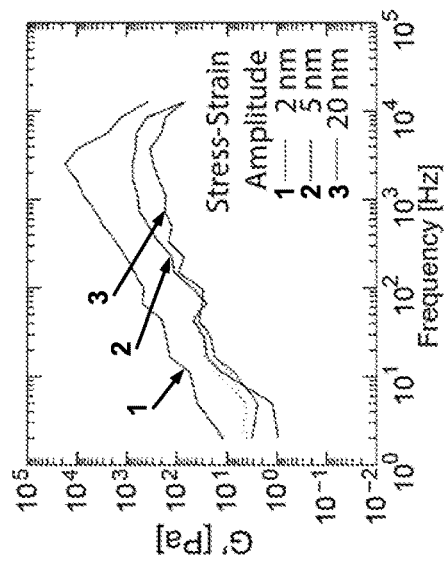

Uncured polydimethylsiloxane (PDMS) was next used as a phantom to test the FFT method in a viscous fluid. For each probe, β and k was calibrated in situ and multiplexed frequency sweeps (2 Hz-12.9 kHz) were performed at stress-strain amplitudes of 2 nm, 5 nm, and 20 nm (trap position displacements) per frequency. FIG. 17 shows the resulting elastic (G') (FIG. 17A) and viscous (G") (FIG. 17B) components and magnitude (G*) of the complex shear modulus (FIG. 17C). Uncured PDMS exhibited nonlinear viscoelasticity, with moduli increasing approximately one order of magnitude with an order of magnitude increase in applied stress-strain amplitude across the frequency range (two-way ANOVA, p<0.0001). The onset of shear thinning occurred at a critical shear rate of ~500 Hz. At 2 Hz, the corresponding complex viscosity η* was approximately 25 Pa·s, 35 Pa·s, and 450 Pa·s at 2 nm, 5 nm, and 20 nm, respectively.

Figure 17F:
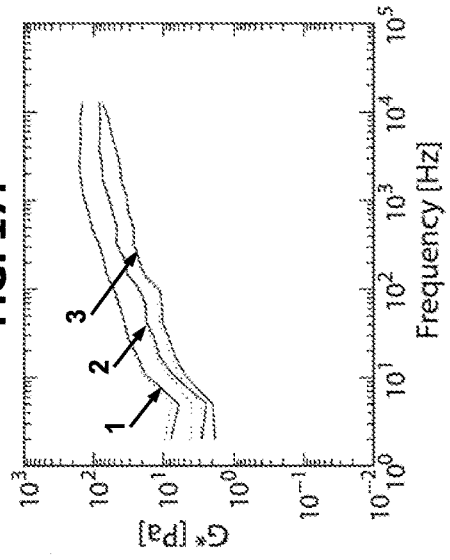
Figure 17E:
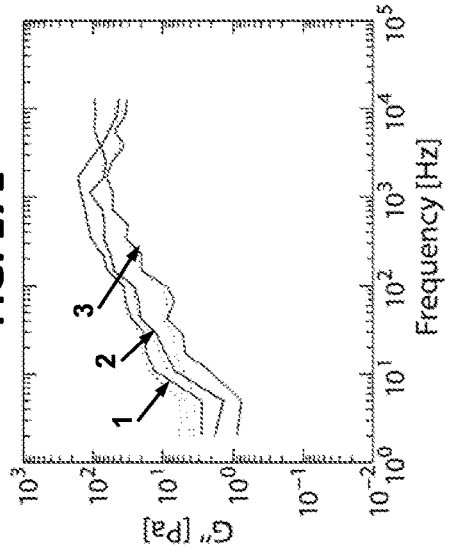
Figure 17D:
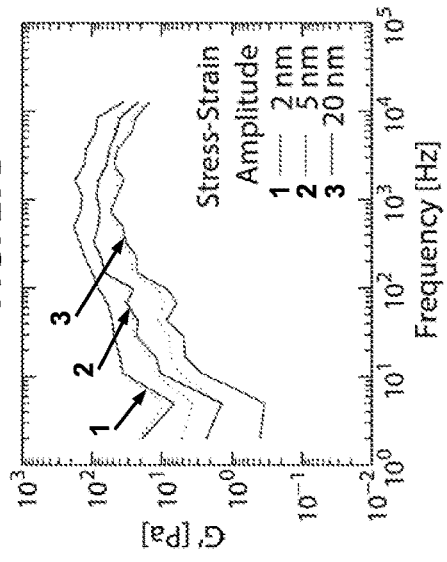

Active microrheology measurements were then performed on the yolks of anaesthetized zebrafish embryos 48 h post fertilization. In order to probe the nonlinear stress-strain response, the trap position was oscillated at stress-strain amplitudes of 2 nm, 5 nm, 10 nm, and 20 nm per frequency. FIG. 17 shows the resulting elastic (G') (FIG. 17D) and viscous (G") (FIG. 17E) components and magnitude (G*) of the complex shear modulus (FIG. 17F). The moduli increase significantly with increased applied stress across the frequency range (two-way ANOVA, p<0.0001). G' increased from ~2 Hz-750 Hz, decreasingly slightly with frequency thereafter. At stress-strain amplitudes of 20 nm, G' rose from 20 Pa-200 Pa, falling again to 35 Pa. The amplitude had greater effect at lower frequencies. G' at 20 nm amplitudes was ~40-fold greater than 2 nm amplitudes at 2 Hz, while only ~4-fold greater at 12.9 kHz. G* increased from 2 Hz-1 kHz, leveling off at higher frequencies. The effect of stress-strain amplitude on G" varied less frequency, with G" at 20 nm amplitudes ~2-3-fold greater than at 2 nm amplitudes. At 20 nm, G" rose from ~2 Pa-100 Pa. The corresponding complex viscosity η* decreased from ~5 Pa·s-0.01 Pa·s at 20 nm and ~1 Pa·s 0.006 Pa·s at 2 nm.

Discussion

In optical trap methods where the sample material properties are unknown and cannot be assumed, some form of direct measurement of the V-nm conversion factor must be conducted. Many materials of interest are both biphasic and feature heterogeneous microdomains of various sizes such that, among a population of monodisperse probes, some are firmly enmeshed or caged by fibers or other solid-phase material, others are free to diffuse, and the remainder are in an intermediate regime of partial confinement. The piezo stage-stepping method for in situ position detection calibration may not be applicable under these circumstances. Furthermore, nonlinear and elastic effects may be present, ruling out many other methods.

This example provides an alternative method to find the V-nm conversion factor of a probe that can be used in liquid or liquid-like material with nonlinear viscoelastic effects, using AOD beam steering of the secondary detection laser across the trapped probe center. The method gives results in good agreement with the power spectrum density and piezo stage stepping methods, and expands the range of materials in which in situ calibration is possible. One caveat is that if the underlying structure of the material influences the detection beam over the length scale of its displacement, then there may be some systematic noise associated with the displacement of the detection beam. This is also true of the piezo method and back focal plane interferometry generally, since it is sensitive not only to scattering by the probe but also to other objects in the beam path. As the detection beam is moved during this calibration process, it may be modulated by scattering from local optical inhomogeneities that introduce a potential source of uncertainty. This possibility was examined by measuring the signal on the detection QPD while oscillating the detection beam in the absence of a trapped probe at a number of random locations. Across the length scale of the oscillation the signals were found to be indistinguishable.

The optical trap method for active microrheology was then applied in the yolks of zebrafish embryos 48 h post fertilization. Physical properties like cell stiffness, viscosity and cortical tension are critical to cell migration, adhesion and division in during embryonic development. Various reports of avian egg viscosity range from $10^{-2}$ Pa·s-1 Pa·s, which is the same range our measurements fall within. Example 1 illustrated measurement of the extracellular matrix viscoelasticity in vivo in zebrafish brain and tail tissue, finding G' and G" rising from ~1 Pa-1 kPa over the frequency range 3 Hz-15 kHz. The example illustrated that the yolk presents similar behavior up to several hundred Hz, but in contrast to the brain and tail tissues, the moduli in the yolk feature a plateau at ~100 Pa from ~750 Hz-12.9 kHz, corresponding to the onset of increased shear thinning The yolk exhibited nonlinear stress-strain response, with as much as 40-fold increase in G' at low frequencies in response to a 10-fold increase in stress-strain amplitude.

It will be apparent that the precise details of the methods or compositions described may be varied or modified without departing from the spirit of the described embodiments. We claim all such modifications and variations that fall within the scope and spirit of the claims below.

It is claimed:

1. A method of assaying viscoelastic properties of a sample, comprising:
   directing a detection beam to a bead embedded in the sample, wherein the bead is an optical trap bead;
   detecting movement of the bead by sensing a position of the detection beam downstream of the bead;
   directing a trap beam on the bead to apply an optical trap to the bead;
   detecting passive movement of the trapped bead due to thermal motion;
   oscillating the trapped bead relative to the sample with a complex waveform comprising a predetermined combination of frequencies, wherein the bead is oscillated along a plane transverse to a path of the detection beam;
   detecting active movement of the trapped bead due to the oscillation; and
   calculating a trap stiffness and a complex modulus for the bead based on the detected passive movement and the detected active movement.

2. The method of claim 1, wherein the complex waveform is composed of a combination of frequencies that provide distinct harmonics.

3. The method of claim 2, wherein the complex waveform comprises:
   a combination of prime frequencies; or
   a combination of frequencies that are a predetermined multiple of prime frequencies.

4. The method of claim 2, wherein the combination of frequencies comprises:
   a set of prime frequencies from 3 to 101 Hz; or
   a set of frequencies from 300 to 15700 Hz that are a predetermined multiple of prime frequencies.

5. The method of claim 2, wherein the combination of frequencies comprises set from 10 to 30 frequencies.

6. The method of claim 1, wherein the combination of frequencies are offset in phase.

7. The method of claim 1, wherein oscillating the trapped bead relative to the sample comprises oscillations in a linear range of viscoelasticity of the sample.

8. The method of claim 1, wherein oscillating the trapped bead relative to the sample comprises oscillations of no more than 200 nm.

9. The method of claim 1, wherein oscillating the bead relative to the sample comprises oscillating the trap beam using an acousto-optic deflector (AOD) when the sample remains stationary.

10. The method of claim 1, wherein oscillating the bead relative to the sample comprises oscillating a nanopositioning stage holding the sample when the trap beam remains stationary.

11. The method of claim 1, wherein the trap beam and the sample are held stable when the passive movement of the trapped bead due to thermal motion is detected.

12. The method of claim 1, wherein the detection beam and the trap beam are directed on the bead through a water immersion objective.

13. The method of claim 12, wherein the water immersion objective has a numerical aperture of about 1.2.

14. The method of claim 1, wherein the position of the detection beam downstream of the bead is sensed using a position sensing detector.

15. The method of claim 14, wherein the position sensing detector is a quadrant photodiode.

16. The method of claim 14, further comprising calculating a change in volts per nm of bead displacement for the position sensing detector.

17. The method of claim 16, wherein calculating the change in volts per nanometer of bead displacement for the position sensing detector comprises:
    stepping the sample through the detection beam using a nanopositioning stage when the optical trap is not applied to the bead; and
    sensing the position of the detection beam downstream of the bead using the position sensing detector.

18. The method of claim 16, wherein determining the change in volts per nanometer of bead displacement for the position sensing detector comprises:
    oscillating the detection beam when the optical trap is applied to the bead; and
    sensing the position of the detection beam downstream of the bead using the position sensing detector.

19. The method of claim 1, wherein the trap beam is a 1064 nm diode laser and the detection beam is a 975 nm diode laser.

20. The method of claim 1, wherein the optical trap comprises a trap power of 1-500 mW and a trap force of 1-10000 Pa.

21. The method of claim 1, wherein the bead is a fluorescent bead and/or is about one µM in diameter.

22. The method of claim 1, wherein the sample is a biological material.

23. The method of claim 22, wherein the biological material is a 3D tissue culture sample.

24. The method of claim 22, wherein the biological material is a tissue sample.

25. The method of claim 24, wherein the tissue sample is a tumor sample.

26. The method of claim 1, comprising assaying the viscoelastic properties of:
    extracellular remodeling during development and cancer metastasis;
    keloid scar formation during wound healing;
    repair and regeneration of injured collagenous tissues such as tendon and cartilage;
    skin stiffening or softening due to aging or other conditions;
    scar formation as scar stiffen or soften due to treatment;
    collagen fibrils and networks in vitro; and/or
    in vivo mechanical mammography.

* * * * *